United States Patent [19]
Scola et al.

[11] Patent Number: 5,821,263
[45] Date of Patent: Oct. 13, 1998

[54] SULFENAMIDE TAXANE DERIVATIVES

[75] Inventors: Paul M. Scola, Glastonbury; Dolatrai M. Vyas, Madison, both of Conn.

[73] Assignee: Bristol-Myers Squibb Company, Princeton, N.J.

[21] Appl. No.: 902,451

[22] Filed: Jul. 29, 1997

Related U.S. Application Data

[60] Provisional application No. 60/026,080 Aug. 26, 1996.

[51] Int. Cl.$^6$ .................... A61K 31/335; A61K 31/44; A61K 31/445; A61K 31/495
[52] U.S. Cl. .................... 514/449; 514/100; 514/232.8; 514/255; 514/320; 514/337; 514/422; 549/218; 549/219; 549/511; 548/525; 546/196; 546/281.7; 544/147; 544/359
[58] Field of Search .................... 548/525; 546/196, 546/281.7; 544/147, 359; 549/218, 219, 511; 514/100, 232.8, 255, 320, 337, 422, 449

[56] References Cited

U.S. PATENT DOCUMENTS

| | | | |
|---|---|---|---|
| 5,453,520 | 9/1995 | Bombardelli et al. | 549/510 |
| 5,496,846 | 3/1996 | Wilson et al. | 514/449 |
| 5,714,512 | 2/1998 | Bastart et al. | 514/449 |

*Primary Examiner*—Amelia Owens
*Attorney, Agent, or Firm*—David M. Morse

[57] ABSTRACT

This invention provides a novel series of taxane derivatives which are characterized by the C3' nitrogen bearing one or two sulfur substituents. The new derivatives are antitumor agents useful in the treatment of such cancers as ovarian, breast, lung, gastric, colon, head and neck, melanoma and leukemia.

11 Claims, No Drawings

SULFENAMIDE TAXANE DERIVATIVES

This application claims benefit of USC Provisional application Ser. No. 60/026,080, filed Aug. 26, 1996.

FIELD OF THE INVENTION

The present invention concerns antitumor compounds. More particularly, the invention concerns novel taxane derivatives, pharmaceutical formulations thereof, and their use as antitumor agents.

BACKGROUND OF THE INVENTION

Taxol (paclitaxel) is a natural product extracted from the bark of Pacific yew trees, *Taxus brevifolia*. It has been shown to have excellent antitumor activity in in vivo animal models and has been approved for the treatment of refractory advanced ovarian cancer and breast cancer. Studies involving other cancers have shown promising results.

A semi-synthetic analog of paclitaxel named Taxotere (docetaxel) has also been found to have good antitumor activity in animal models and has recently been approved for use in patients with locally advanced or metastatic breast cancer. The structures of paclitaxel and docetaxel are shown below along with the conventional numbering system of taxane molecules; such numbering system is also employed in this application.

Taxol (paclitaxel): R=Ph; $R^1$=acetyl

Taxotere (docetaxel): R=t-butoxy; $R^1$=hydrogen

SUMMARY OF THE INVENTION

The present invention relates to a novel class of taxane derivatives. More particularly, the derivatives are characterized by having at the 3'carbon a moiety of the formula $$R^2\diagdown N \diagup R^3$$

wherein $R^2$ and $R^3$ are each independently hydrogen or a sulfenamide of the formula —$SR^y$ in which $R^y$ is aryl, substituted aryl, heteroaryl, substituted heteroaryl or optionally substituted $C_{1-6}$ alkyl, providing that $R^2$ and $R^3$ may not both be hydrogen.

A preferred embodiment of the present invention comprises compounds of the formula wherein
$R^1$ is $C_{1-6}$ alkyl, $C_{2-6}$ alkenyl, $C_{3-6}$ cycloalkyl or a radical of the formula —W—$R^x$ in which W is a bond, $C_{2-6}$ alkenediyl or —$(CH_2)_t$— in which t is an integer of from one to six and $R^x$ is naphthyl, phenyl or heteroaryl, said $R^x$ group being optionally substituted by 1 to 3 same or different $C_{1-6}$ alkyl, $C_{1-6}$ alkoxy, halogen or —$CF_3$ groups;

$R^2$ and $R^3$ are each independently hydrogen or a sulfenamide of the formula —$SR^y$ in which $R^y$ is aryl, substituted aryl, heteroaryl, substituted heteroaryl, $C_{1-6}$ alkyl having a terminal $C_{1-6}$ alkoxy or $C_{1-6}$ alkanoyloxy group and being optionally substituted by an oxo group, or $C_{1-6}$ alkyl substituted by both a carboxyl and amino groups, providing that $R^2$ and $R^3$ may not both be hydrogen;

$R^4$ is hydrogen, hydroxy or —$C(O)CH_3$;
$R^5$ is hydrogen, hydroxy, —O—$C_{1-6}$ alkyl,
—$C(O)R_a$, —$OC(O)OR_a$, —$OC(O)NHR_a$,
—$OC(O)NR_bR_c$, —$OCH_2OR^1$ wherein $R^1$ is as defined above,
—$OCHR_aOR^1$ where $R^1$ is as defined above,
—$OCH_2SCH_3$, —$OCH_2OCH_2SCH_3$, —$OP(O)(OH)_2$,
—$OCH_2OP(O)(OH)_2$, —$OCH_2OCH_2OP(O)(OH)_2$,
—$OC(R_a)_2 SR^1$ where $R^1$ is as defined above, or
—$OCHR_aSR^1$ where $R^1$ is as defined above;

$R_a$ is $C_{1-6}$ alkyl, $C_{2-6}$ alkenyl, $C_{2-6}$ alkynyl or $C_{3-6}$ cycloalkyl, any of which groups can be optionally substituted with one to six of the same or different halogen atoms;

$R_b$ and $R_c$ are each independently hydrogen, —$CH_3$, —$CH_2CH_2$— or benzyl, or $R_b$ and $R_c$ together with the nitrogen of $NR_bR_c$ form a pyrrolidino, piperidino, morpholino or N-methylpiperazino group;

$R^6$ and $R^7$ are each independently hydrogen, hydroxy, $C_{1-6}$ alkyl or $R^5$, or $R^5$ and $R^6$ form an epoxide and $R^7$ is hydrogen, or $R^5$ and $R^6$ form a bond and $R^7$ is hydrogen;

$R^{19}$ is methyl or hydroxymethyl, or $R^{19}$ and $R^5$ together can form a cyclopropane ring in which case $R^6$ and $R^7$ are both hydrogen;

$R^8$ is $$-O\diagdown \underset{R_d}{\overset{L}{\diagup}}$$

where L is O or S and $R_d$ is $C_{1-6}$ alkyl, $C_{2-6}$ alkenyl, $C_{2-6}$ alkynyl, $C_{3-6}$ cycloalkyl, $C_{3-6}$ cycloalkenyl, heteroaryl, —O—$C_{1-6}$ alkyl, —O—$C_{2-6}$ alkenyl, —O—$C_{2-6}$ alkynyl, —$CH_2OCH_3$, —$CH_2OCH_2OCH_3$, —$CH_2OCH_2OCH_2CH_3$, —$CH_2CH_2OCH_3$, or —S—$C_{1-6}$ alkyl; and $R^9$ is aryl, substituted aryl, cycloalkyl, $C_{1-6}$ alkyl, heteroaryl or substituted heteroaryl; and pharmaceutically acceptable salts thereof.

Another aspect of the present invention provides a method for inhibiting tumor growth in a mammalian host which comprises administering to said mammalian host an antitumor effective amount of a compound of the present invention.

Yet another aspect of the present invention provides a pharmaceutical formulation (composition) which comprises an antitumor effective amount of a compound of the present invention and a pharmaceutically acceptable carrier.

DETAILED DESCRIPTION OF THE INVENTION

In the application, unless otherwise specified explicitly or in context, the following definitions apply:

"Ph" means phenyl.

"Ac" means acetyl.

"Alkyl" means a straight or branched saturated hydrocarbon chain having the indicated number of carbon atoms, e.g. ($C_1$–$C_6$)alkyl means a chain having from one to six carbon atoms; examples include methyl, ethyl, n-propyl, isopropyl, n-butyl, sec-butyl, isobutyl, t-butyl, n-pentyl, sec-pentyl, isopentyl and n-hexyl.

Depending on the context, "($C_1$–$C_6$)alkyl" can also refer to ($C_1$–$C_6$)alkylene which bridges two groups; examples include propane-1,3-diyl, butane-1,4-diyl, 2-methylbutane-1,4-diyl, etc.

"Alkenyl" means a straight or branched hydrocarbon chain having at least one carbon—carbon double bond and having the indicated number of carbon atoms, e.g. ($C_2$–$C_6$)alkenyl; examples include ethenyl, propenyl, isopropenyl, butenyl, isobutenyl, pentenyl and hexenyl. Depending on the context "($C_2$–$C_6$)-alkenyl" can also refer to $C_2$–$C_6$ alkenediyl which bridges two groups; examples include ethylene-1,2-diyl(vinylene), 2-methyl-2-butene-1,4-diyl, 2-hexene-1,6-diyl, etc.

"Alkynyl" means a straight or branched hydrocarbon chain having at least one carbon—carbon triple bond and having the indicated number of carbon atoms, e.g. ($C_2$–$C_6$)alkynyl; examples include ethynyl, propynyl, butynyl and hexynyl.

"Cycloalkyl" means a cyclic saturated hydrocarbon group, e.g., $C_3$–$C_6$cycloalkyl refers to cyclopropyl, cyclopentyl or cyclohexyl.

"Cycloalkenyl" means a cyclic hydrocarbon group (cycloalkyl) further containing at least one carbon—carbon double bond forming a partially unsaturated ring.

"Alkoxy" refers to straight or branched alkyloxy groups such as methoxy, ethoxy, n-propoxy, i-propoxy, n-butoxy, t-butoxy, n-pentyloxy, n-hexyloxy or 3-methylpentyloxy.

"Halogen" means fluorine, chlorine, bromine or iodine.

"Alkanoyloxy" refers to groups such as

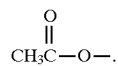

"Pharmaceutically acceptable salt" means nontoxic pharmaceutically acceptable acidic and/or basic salts formed with inorganic and/or organic acids and bases. Illustrative acidic salts are salts formed with mineral acids such as HCl, $H_2SO_4$ or $HNO_3$, or carboxylic acids such as trifluoroacetic acid or acetic acid. Illustrative basic salts include salts formed with amines such as triethylamine, diisopropylethylamine or pyridine, or amino acids such as arginine or guanidine. Salts of hydroxyl groups such as metal (i.e., alkali or alkaline earth metal) alkoxides are also contemplated as "salts" herein. Such pharmaceutically acceptable salts may be prepared according to conventional chemical methods (see, for example, WO 96/00724).

"Aryl" means aromatic hydrocarbon having from 6 to 10 carbon atoms; examples include phenyl and naphthyl.

"Substituted aryl" means aryl substituted with at least one group selected from ($C_1$–$C_6$)alkanyloxy, hydroxy, halogen (fluorine, chlorine, bromine, iodine), ($C_1$–$C_6$)alkyl, trifluoromethyl, ($C_1$–$C_6$)alkoxy, aryl, ($C_2$–$C_6$)alkenyl, ($C_1$–$C_6$)alkanoyl, nitro, amino, ($C_1$–$C_6$)dialkylamino or ($C_1$–$C_6$)alkylthio.

"Heteroaryl" means a 5- or 6-membered aromatic ring containing at least one and up to four non-carbon atoms selected from oxygen, sulfur and nitrogen. Examples of heteroaryl include thienyl, furyl, pyrrolyl, imidazoyl, pyrazolyl, thiazolyl, isothiazolyl, oxazolyl, isoxazolyl, triazolyl, thiadiazolyl, oxodiazolyl, tetrazolyl, pyridyl, pyrimidyl, pyrazinyl, pyridazinyl, triazinyl and tetrazinyl.

"Substituted heteroaryl" means heteroaryl substituted with at least one substituent group mentioned above in connection with "substituted aryl".

A preferred embodiment of the present invention are compounds of the formula

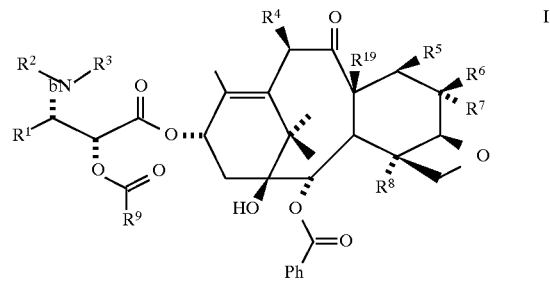

wherein $R^1$ is phenyl, p-fluorophenyl, isobutenyl, isobutyl, 2-furyl, cyclopropyl or isopropyl;

$R^2$ is hydrogen and $R^3$ is —$SR^y$ in which $R^y$ is aryl, substituted aryl, heteroaryl, substituted heteroaryl or $C_{1-6}$ alkyl substituted by both a carboxyl and amino group;

$R^4$ is —$C(O)CH_3$;

$R^5$ is hydrogen, hydroxy, —$OCH_2OCH_3$, —$OCH_2SCH_3$ or —$OC(O)OR_a$ in which $R_a$ is $C_{1-6}$ alkyl;

$R^6$ and $R^7$ are each independently hydrogen, hydroxy or —$OCH_2OCH_3$;

$R^{19}$ is methyl or hydroxymethyl, or $R^{19}$ and $R^5$ together can form a cyclopropane ring in which case $R^6$ and $R^7$ are both hydrogen; and $R^8$ is

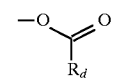

in which $R_d$ is $C_{1-6}$ alkyl, $C_{3-6}$ cycloalkyl or —O—$C_{1-6}$ alkyl; and pharmaceutically acceptable salts thereof.

A still further preferred embodiment of the present invention are compounds of the formula

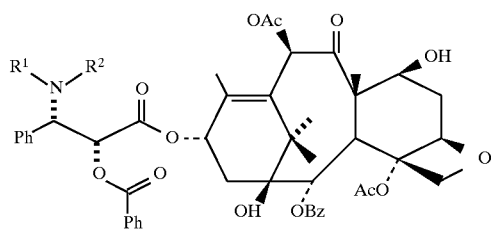

wherein $R^1$ and $R^2$ are either both

or $R^2$ is hydrogen and $R^1$ is

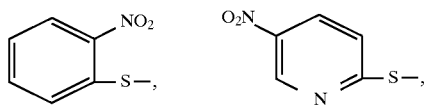

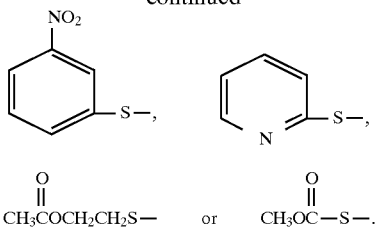

The compounds of the present invention may be prepared by reacting an appropriate intermediate of the formula

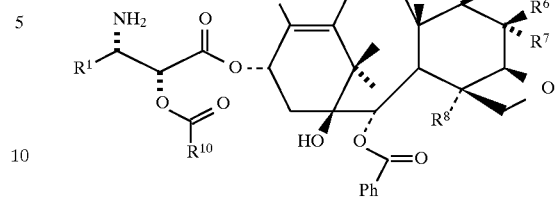

with a sulfenyl halide in an inert aprotic solvent such as tetrahydrofuran (THF) or methylene chloride under basic conditions. Scheme I below illustrates a typical procedure:

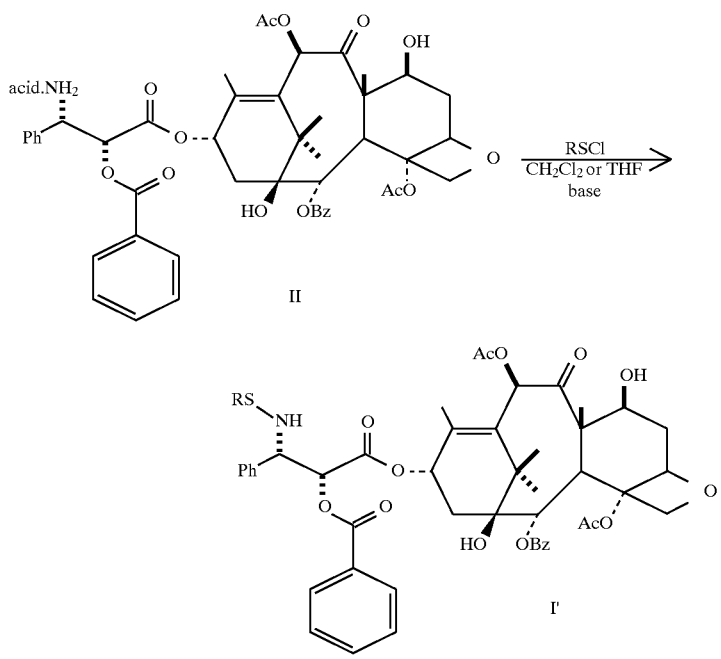

The sulfenyl chlorides are either commercially available or are generated from the corresponding disulfide using conventional reactions. Preparation of starting materials II is described in WO 94/14787. Briefly, they are made by steps comprising:

(a) coupling the oxazoline of the formula III

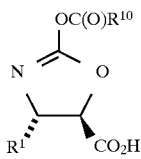

with C13-hydroxy of taxane of formula IV

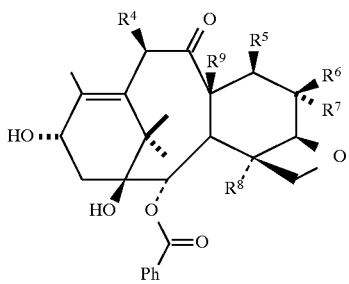

to afford a compound of formula V

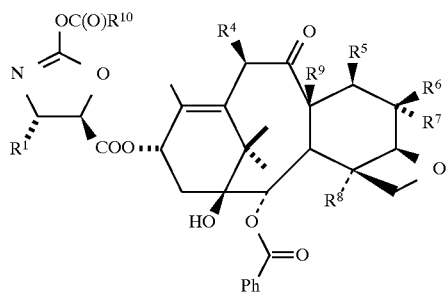

and (b) contacting a compound of formula V with an acid capable of opening the oxazoline ring of said compound of the formula V to afford a compound of formula II or salt thereof. Oxazolines of formula III are already well described in PCT application WO 94/14787 published Jul. 7, 1994.

In formulae III, IV and V above, $R^1$, $R^4$, $R^5$, $R^6$, $R^7$, $R^8$, $R^9$ and $R^{10}$ are as previously defined.

For preparation of 7-ether paclitaxel analogs, see PCT application WO 96/004 published Jan. 11, 1996 and European Patent Application 694,539 A1 published Jan. 31, 1996.

The procedures for preparing taxane derivatives which contain substituents at C-6 and which are deoxygenated at C-7 are disclosed in our colleague's co-pending application Ser. No. 60/019,493 filed Jun. 6, 1996; the disclosure of which is herein incorporated by reference in its entirety. The 7-deoxy-6 substituted taxanes described by this invention can be prepared as described above by coupling the appropriately substituted 7-deoxy-6-substituted baccatin derivative IV with the appropriate oxazoline III and then proceeding to compounds I as described above. The baccatin derivatives IV should be protected in such a manner that the only reactive hydroxy groups are the ones at position 13 and 1 of the taxane core. The following representative procedures give examples for the preparation of C-7 deoxy-6-hydroxy taxane derivatives, the preparation of the corresponding baccatin derivatives via sidechain cleavage, and the preparation of suitably protected baccatin derivatives IV which can be utilized for coupling to paclitaxel sidechains or for use in this invention with the oxazoline acid III.

The 7-deoxy-6-deoxy-taxane derivatives can be prepared from the previously reported 6,7-diol intermediate 4 (Scheme II) or suitably substituted analogs. The preparation of this diol intermediate is shown in Scheme II below.

As shown in Scheme II, the starting material is a taxane analog suitably protected to leave the most reactive hydroxy group at C-7. Compound 1 in Scheme II is protected at the 2' hydroxy group at the sidechain. The two examples of compound 1 actually described utilize silyl protecting groups at the 2' position, but other protecting groups could be utilized. The preparation of intermediates 1 are now well known in the art. The synthesis of diols 4 utilizes precursor 6,7-olefin analogs 3 which are also now known in the art. The compounds 3 can be formed directly from intermediates 1 upon treatment with a reagent such as DAST as described in the U.S. Pat. No. 5,380,751. The synthesis of olefin 3 described in Scheme II proceeds through the 7-trifluoromethanesulfonate (triflate) intermediates 2 which are prepared as shown in step A. Elimination of the triflate (step B) provides the desired olefins 3. The preparation of 7-O triflates and their conversion into cyclopropanes and olefins has been divulged by Johnson, R. A., et al., *Taxol chemistry. 7-O-Triflates as precursors to olefins and cyclopropanes. Tetrahedron Letters,* 1994. 35(43): p. 7893–7896 & by the same authors in WO 94/29288.

The olefin 3 is then hydroxylated with osmium tetroxide (step C) which is used in either stoichiometric quantities or catalytically in the presence of a cooxidant such as N-methyl morpholine-N oxide (NMO). A patent application on such diol intermediates which includes some methods of its preparation has been published: Roth et. al., 6,7 EPO 600 517 A1. A protected taxane diol intermediate has also been described in the literature by Liang et. al. *Tetrahedron Letters* 1995, 36(17) 2901–2904. and ibid. 1995, 36(43) 7795–7798. The osmium reagent only reacts from the face of the double bond which is down or α as the taxane core is depicted in this document. Thus this reaction provides only one stereoisomer.

The preferred approach to the initial 7-deoxy-substituted taxanes is shown in Scheme III. An advantage of this approach is it avoids the need for a selective protection of the starting 6,7 diol 4. A new cyclic thiocarbonate 5 is formed (step D) upon reaction with thiocarbonyldiimidazole (or alternatively thiophosgene could be used) under standard conditions of amine base and optional inert solvent. Other standard organic chemistry bases could also be utilized. Reduction of the thiocarbonate 5 (step E) with most preferably, a trialkyl germane such as tri-n-butyl germane, provides the C-7 deoxy compound 6 with little, if any, competitive formation of the C-6 deoxy material. Alternatively, a trialkyl tin hydride could be utilized in place of the germanium reagent. The use of the tin hydride reagent also results in competitive deoxygenation at C-10 which produces mixtures which must be separated. The tin reagent is the method of choice for producing C 7 and 10 deoxy 6-substituted analogs if these are the desired targets. The use of trialkyl germane to suppress an unwanted side reaction is not precedented. This reagent has been studied by physical chemists in other radical reactions. J. W. Wilt et. al. *J. Am. Chem. Soc.* 1988, 110, 281–287. The product of step E is a 7-deoxy-6α-hydroxy intermediate 6 which is protected at the sidechain. As shown in Scheme III, deprotection (step F) of the sidechain by standard methods which are now well known in the art provides compounds VI ($R^6$=—H, $R^7$=—OH)

As shown in Scheme IV, the C-6 alcohol 6 can now be oxidized to the ketone 11 using standard oxidants common in the art. The preferred reagent is TPAP (Tetrapropylammonium perruthenate) as described by Ley in *Aldrichimica Acta* 21(1), 16(1988), and ibid., 22(2), 53

(1989) and *J. Chem. Soc. Chem. Commun.* 1625(1987). This ketone can then be desilylated under a variety of standard conditions to provide compounds VI ($R^6=R^7=$oxo (=O)).

Reduction of ketone 11 with standard reducing agents such as sodium borohydride in ethanol under conditions where selective ketone reduction occurs in the presence of esters (or the more hindered C-9 ketone) produces the protected 6-β-hydroxy-7-deoxy paclitaxel 12 (Scheme V). Hydride delivery occurs preferentially from the bottom, less hindered a face. Desilylation of compound 12 provides 6β-hydroxy compounds VI ($R^6=$—OH, $R^7=$—H).

As shown in Scheme VI, addition of organometallic reagents to the ketone 11 provides mainly or exclusively tertiary alcohols at C-6 with the alcohol in the beta configuration (up). This is a result of more facile attack from the bottom face. For example use of trimethyl aluminum provides compound 13 ($R^6=$—OH, $R^7=$—CH$_3$), which is the product of methyl addition to the ketone. Other organometallic reagents such as alkyl lithium reagents, Grignard reagents, or cerium based reagents which are well known in the art would also provide some of the desired products. Desilylation provides compounds VI ($R^6=$—OH, $R^7=$—CH$_3$).

As shown in Scheme VII of the experimental section, reductive removal of the C-13 sidechain using tetrabutylammonium borohydride via standard paclitaxel methodology (N. F. Magri, D. G. I. Kingston, C. Jitrangsri, T. Piccariello J. Org. Chem. 1986, 51, 3239–3242) from diol VI ($R^6=$—H, $R^7=$—OH) provides the alpha hydroxy baccatin IV-z which can be selectively protected using standard protecting groups on the 6-hydroxy group to give IV-y. The examples utilize trialkylsilyl ethers as the protecting group but others are also suitable. Protected baccatin IV-y can now be coupled with other sidechains using any methodology which is well known in the art. Similar methodology can be utilized to prepare baccatin analogs possessing varying substitution patterns at the C-6 position. In these examples, lactams with alternative sidechains are employed by using the standard coupling which has been described in U.S. Pat. Nos. 5,229,526 and 5,175,315 by Holton to produce compounds 9. Desilylation (or suitable deprotection conditions) provides analogs VI ($R^6=$—H, $R^7=$—OH)

As shown in Scheme VIII direct oxidation of the 6α-alcohol of analogs VI ($R^6=$—H, $R^7=$—OH) followed by reduction as described above in Scheme VI, provides 6 beta-hydroxy analogs with modified sidechains. Alternatively, as shown in Scheme IX, bis silylated compounds 9 can be selectively deprotected at C-6 using, for example, acidic Dowex resin suspended in methanol (step w) to provide intermediates 6 which can be oxidized and reduced as described in Schemes IV and V. This produces compounds VI ($R^6=$—OH, $R^7=$—H) with a 6β-hydroxy substituent and modified sidechains.

As shown in Scheme X, step X, deprotonation of alcohols 17 with a lithium amide base (lithium bistrimethylsilylamide) followed by O-alkylation with bromomethyl methyl ether provides the 6α-methoxymethyl ether analog 17. This reaction illustrates the preparation of hydroxy derivatives at C-6 and demonstrates that conventional alcohol derivatization techniques can be utilized with C-6 alcohols. Other derivatives claimed in this application can be prepared using similar methodology. Deprotection of the 2' hydroxy protecting group under standard conditions, provides the 6-methoxymethyl ethers VI ($R^6=$—OCH$_2$OCH$_3$, $R^7=$—OH). As shown in Scheme XI, a similar sequence can be utilized to derivatize 6β-alcohols and in this case produced the 6β-methoxymethyl ether analogs VI ($R^6=$—OCH$_2$OCH$_3$, $R^7=$—H).

In formulae VI above $R^1$, $R^4$, $R^5$, $R^6$, $R^7$, $R^8$, $R^9$ and $R^{10}$ are as previously defined.

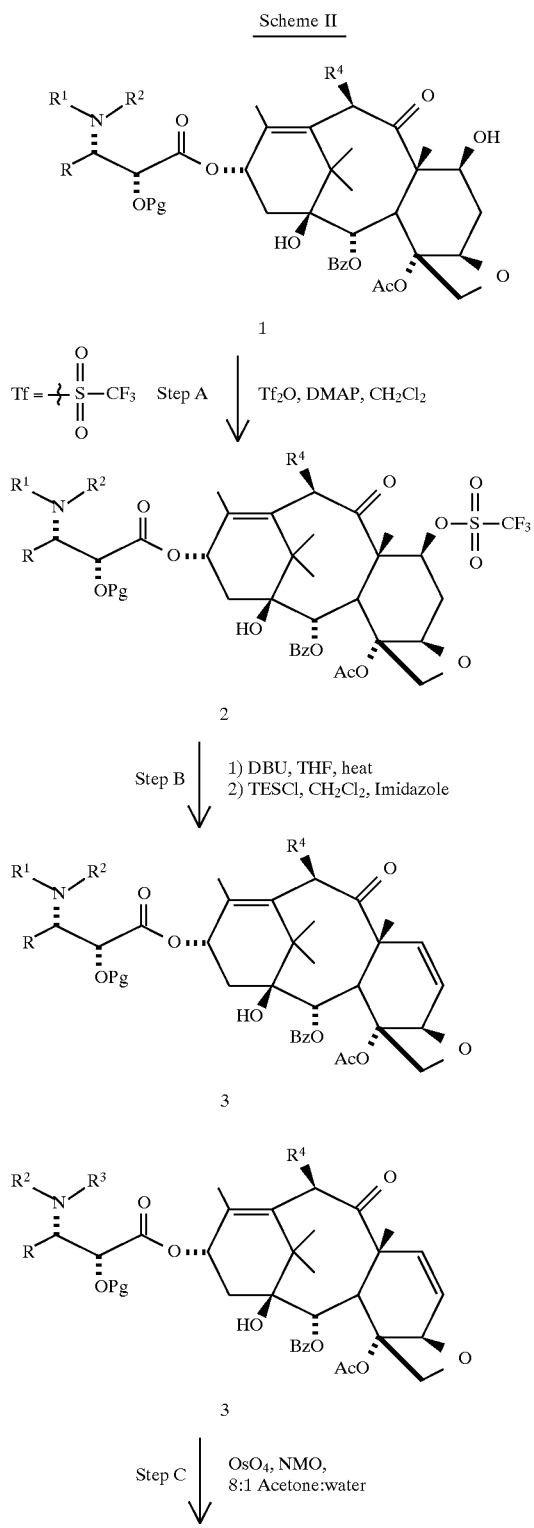

Scheme II

Scheme II
-continued
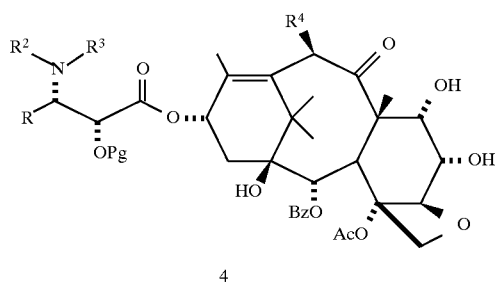
4
Scheme III
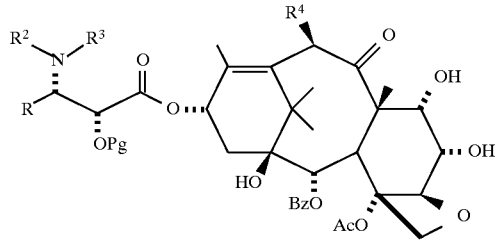
4
step D ↓ (thiocarbonyldiimidazole), DMAP
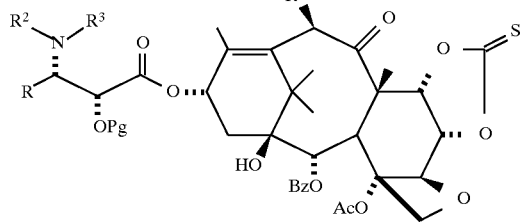
5
step E ↓ Bu₃GeH, AIBN, Toluene 80° C.
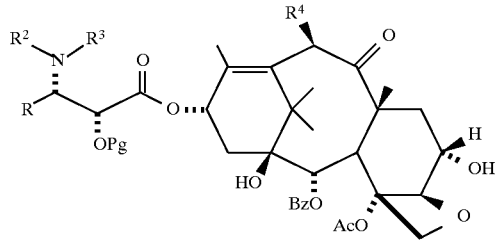
6
Scheme III
-continued
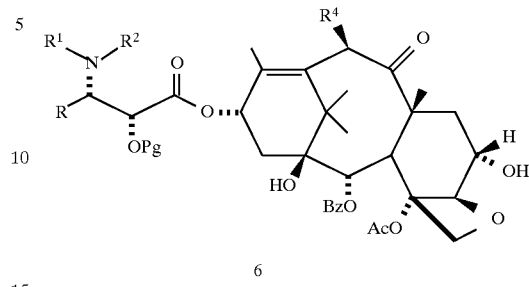
6
step F ↓ Protecting Group removal
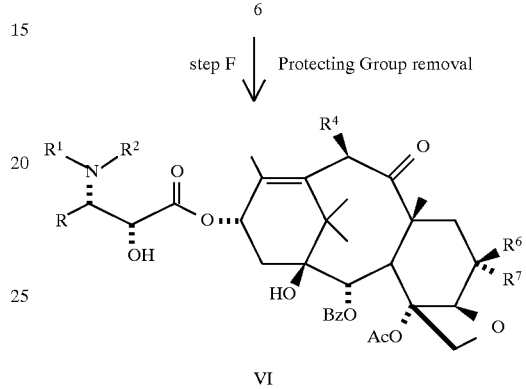
VI
$R^6 =$ —H, $R^7 =$ —OH
Pg = Protecting group
Scheme IV
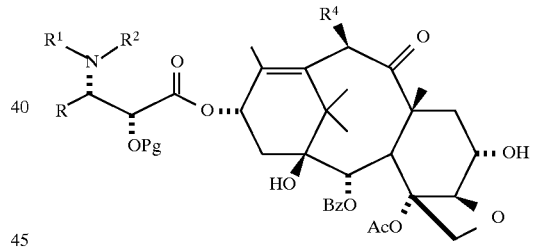
6
step K ↓
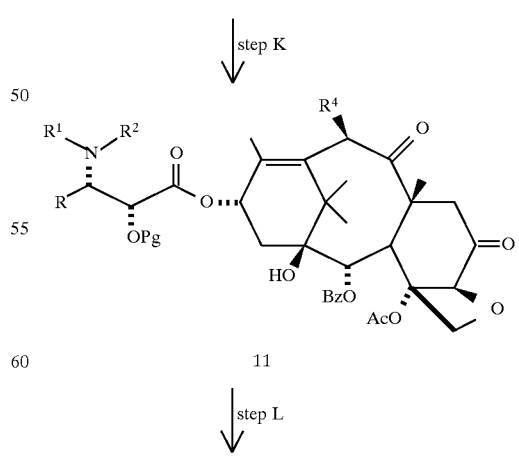
11
step L ↓

Scheme IV
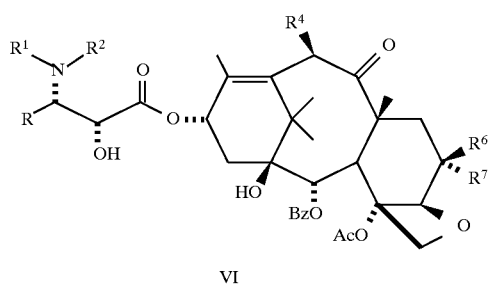
VI
R⁶ = R⁷ = =O (oxo)
Scheme V
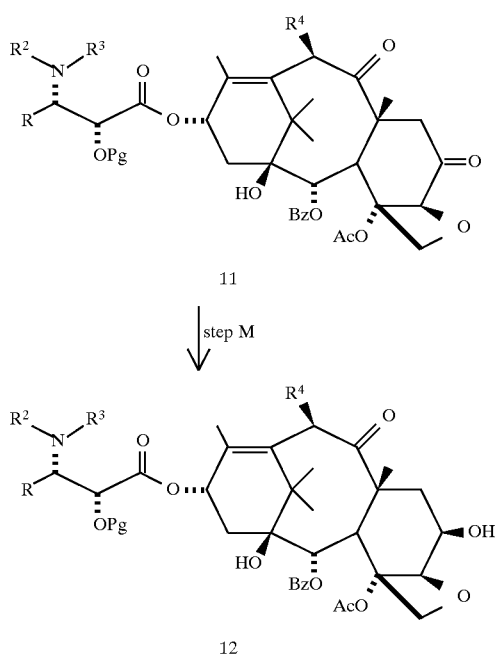
Scheme VI
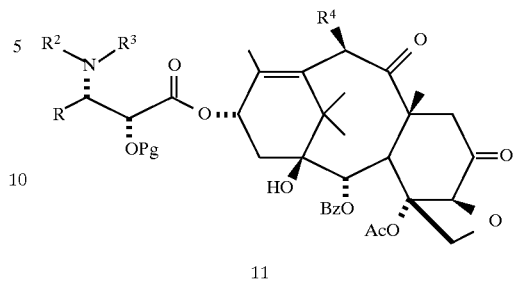
↓ step O
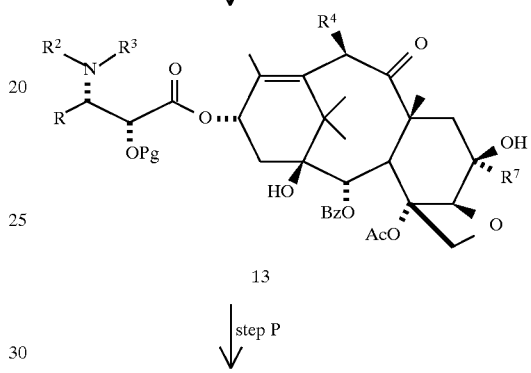
↓ step P
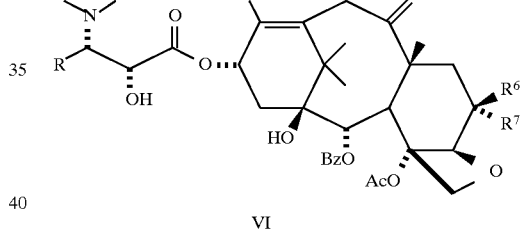
VI
R⁶ = —OH, R⁷ = —CH₃
Scheme VII
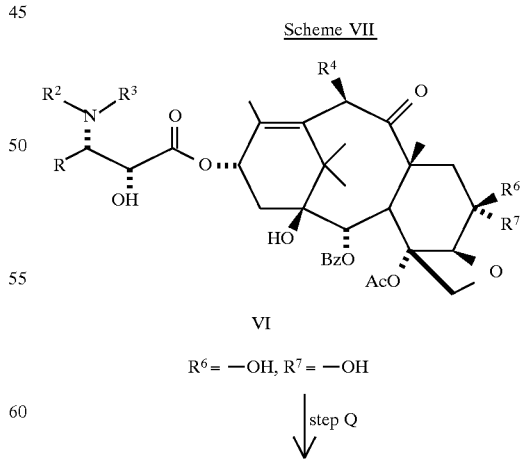
VI
R⁶ = —OH, R⁷ = —OH
↓ step Q -continued
Scheme VII
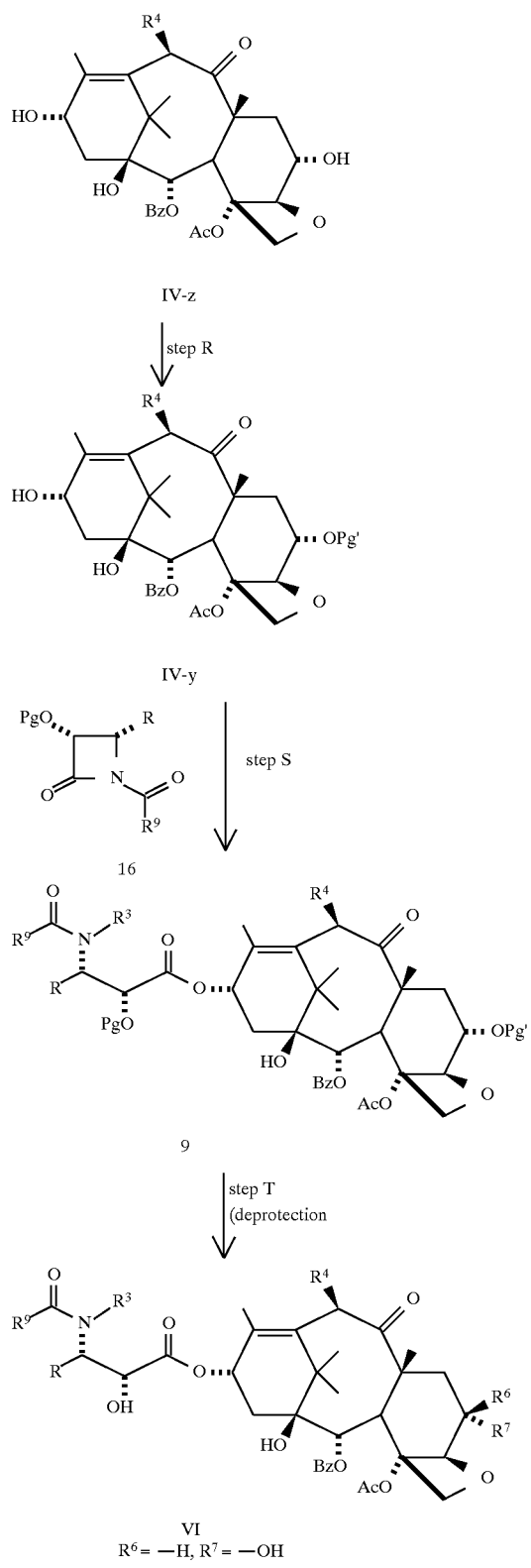
Scheme VIII
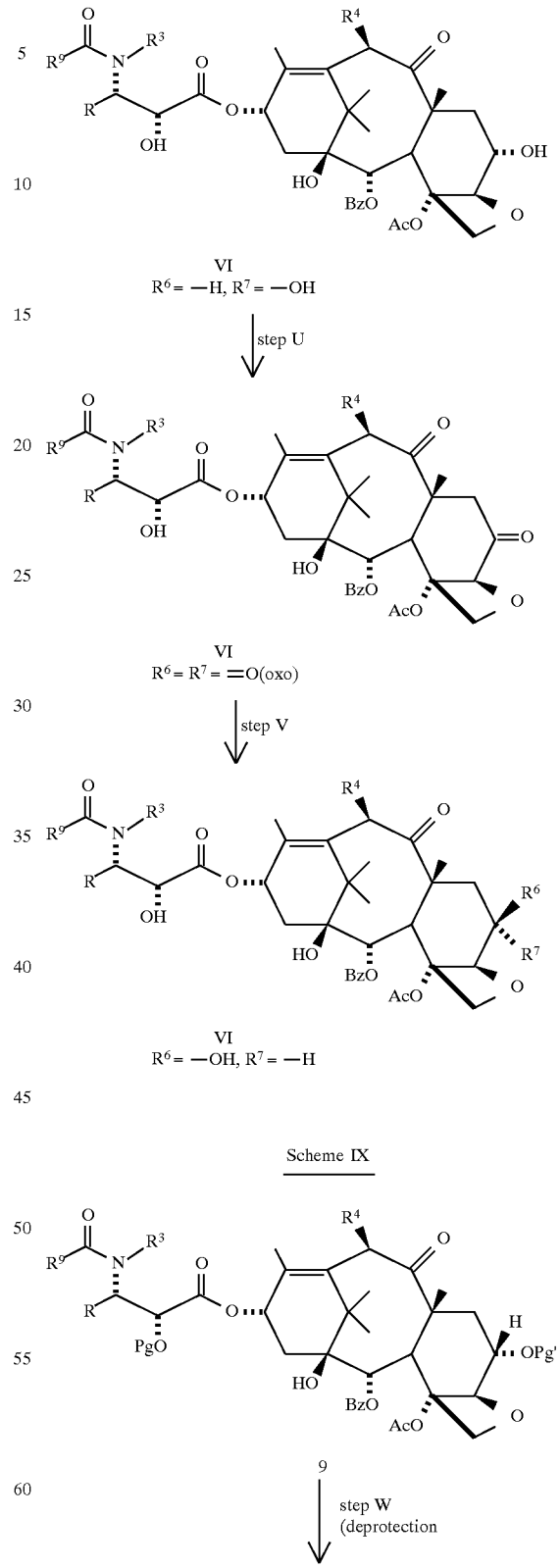

Scheme IX

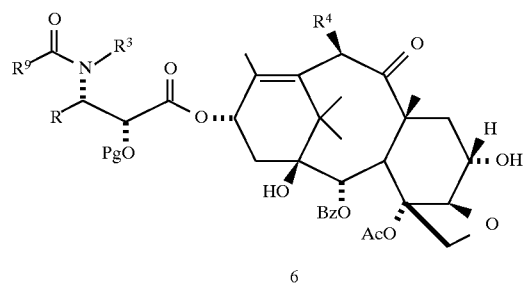

6

Scheme X

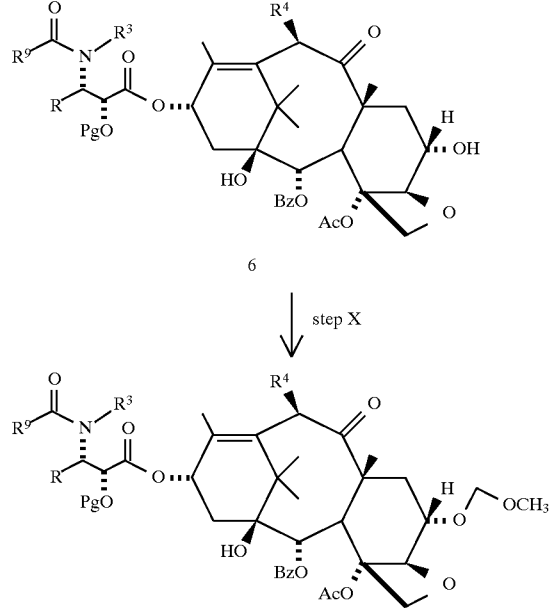

Scheme XI

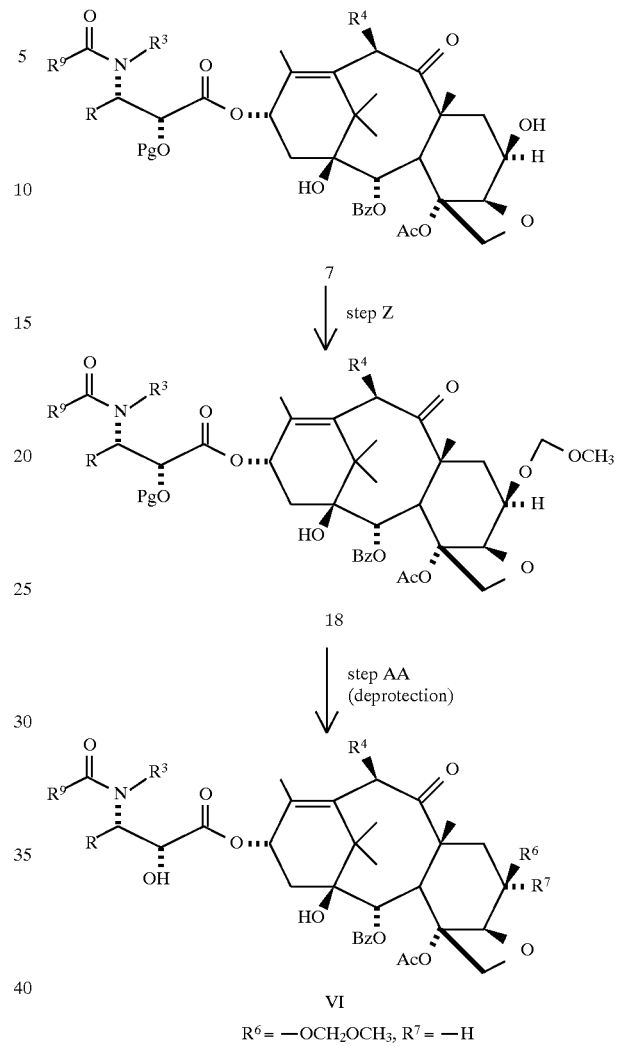

By now there are many publications teaching the conversion of paclitaxel taxane core substitutents into other groups. Using these established methods or obvious variants thereof, many taxanes of formula I can be readily made. The following citations are only representative examples and do not cover all the literature methods which could be utilized for preparing compounds I. For example, for transforming C4-acetoxy into other functional groups see, S. H. Chen et al., *J. Organic Chemistry*, 59, pp 6156–6158 (1994) and PCT application WO 94/14787 published Jul. 7, 1994; for converting C2-benzoyloxy to other groups see, S. H. Chen et al., *Bioorganic and Medicinal Chemistry Letters*, Vol. 4, No. 3, pp 479–482 (1994) and European Patent Application 617,034A1 published Sep. 28, 1994; for modifying C10-acetyloxy see, J. Kant et al, *Tetrahedron Letters*, Vol. 35, No. 31, pp 5543–5546 (114) and U.S. Pat. No. 5,294,637 issued Mar. 15, 1994; for making C10 and/or C7 unsubstituted (deoxy) derivatives see, European Patent Application 590, 267 A2 published Apr. 6, 1994 and PCT application WO 93/06093 published Apr. 1, 1993; for making 7,8-cyclopropyl, 6,7-dihydroxy and 6,7-olefinic groups see, R. A. Johnson, *Tetrahedron Letters,* Vol. 35, No. 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingtston, *Tetrahedron Letters,* Vol. 36, No. 17, pp 2901–2904 (1994); for making C7-epi-fluoro see, G. Roth et al., *Tetrahedron Letters,* Vol. 36, pp 1609–1612 (1993); for forming C7 esters and carbonates see, U.S. Pat. No. 5,272,171 issued Dec. 21, 1993 and S. H. Chen et al., *Tetrahedron,* 49, No. 14, pp 2805–2828 (1993); for 9-dihydro taxanes see, L. L. Klein, *Tetrahedron Letters,* Vol 34, No 13, pp 2047–2050 (1993), PCT application WO 94/08984 published Apr. 28, 1994, U.S. Pat. No. 5,352,806 issued Oct. 4, 1994 and PCT application WO 94/20485 published Sep. 15, 1994. The examples which follow provide more elaboration on the preferred reaction conditions.

Description of Specific Embodiments

The specific preparations and examples that follow are meant to illustrate the synthesis of the compounds of the present invention and are not to be construed as limiting the scope of the invention.

In the following experimental procedures, all temperatures are understood to be in Centigrade (C) when not specified. The nuclear magnetic resonance (NMR) spectral characteristics refer to chemical shifts (() expressed in parts per million (ppm) versus tetramethylsilane (TMS) as reference standard.

The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

The abbreviations used herein are conventional abbreviations employed in the art. Some of the abbreviations used are: THF (tetrahydofuran), DMAP (4-dimethylaminopyridine), h (hour), TLC (thin layer chromatography), EtOAc (ethyl acetate), Py (pyridine), Ac (acetyl), Ph (phenyl), TES (triethylsilyl), Tf=triflate=trifluoromethanesulfonate, AIBN (azaisobutyrylnitrile), EtOH (ethanol), DBU (1,8-diazabicyclo[5.4.0]undec-7-ene), $Bu_3GeH$ (tributylgermane), LIHMDS (lithium bis (trimethylsilyl)amide), TPAP (tetrapropylammonium perruthenate), $Bu_3SnH$ (tributyltin hydride), $Bu_4NF$ (tetrabutylammonium fluoride), NMO (4-methylmorpholine-N-oxide) and MOMBr (methoxymethyl bromide).

Preparation of Starting Materials—Scheme II

2'-O-(triethylsilyl)-paclitaxel [1a]

Paclitaxel (15 g, 17.57 mmol) was dissolved in a solution of 60 mL of pyridine and 60 mL of dichloromethane and then the mixture was cooled to 0° C. Triethylsilyl chloride (11.8 mL, 70.3 mmol) and the reaction was stirred for 90 min at 0°. The reaction was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.0 g (99%) of the title compound.

2'-O-(t-butyldimethylsilyl)-paclitaxel [1b]

Paclitaxel (146.0 mg, 0.17 mmol) was dissolved in dry N,N-dimethylformamide (1 mL). To this solution imidazole (116.1 mg, 1.7 mmol) and t-butyldimethylsilyl chloride (128.8 mg, 0.85 mmol) were added successively and the mixture was stirred at 60° C. for 1 hour. The reaction mixture was then diluted with ethyl acetate (2 mL), followed by water. The aqueous layer was washed with additional ethyl acetate (2×2 mL). The combined organic layers were then washed with water and brine, dried over sodium sulfate, and evaporated to give crude product. Purification of the crude product by preparative TLC (silica gel, 7:3 hexane:ethyl acetate) furnished 2'-O-(t-butyldimethylsilyl)-paclitaxel (157 mg, 95% yield).

2'-O-(triethylsilyl)-7β-O-trifluoromethanesulfonylpaclitaxel [2a]

The alcohol 1a (17 g, 17.5 mmol) and DMAP (8.55 g, 70 mmol) was dissolved in dichloromethane and then the mixture was cooled to 0° C. Trifluoromethanesulfonic anhydride (3.39 mL, 20.1 mmol) was added via syringe and then reaction was allowed to warm to ambient temperature. The reaction was stirred for 2 hours, was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.6 g (91%) of the title compound.

2'-O-(t-Butyldimethylsilyl)-7β-O-trifluoromethanesulfonylpaclitaxel [2b]

2'-O-(t-butyldimethylsilyl)paclitaxel [1b] (180.0 mg, 0.19 mmol) was dissolved in dry $CH_2Cl_2$ (2 mL). To this solution 4-dimethylaminopyridine (61.0 mg, 0.5 mmol) and trifluoromethanesulfonyl chloride (50 mL, 0.5 mmol) were added successively at 0° C. and the mixture was stirred at room temperature for 1 hour. Then to this solution additional 4-dimethylamino pyridine (61.0 mg, 0.5 mmol) and trifluoromethanesulfonyl chloride (50 mL, 0.5 mmol) were added successively and the mixture was stirred at room temperature for additional 1.5 hours. The reaction mixture then was diluted with EtOAc (4.0 mL) and the precipitate was filtered off on Celite. The solvent was evaporated, and the residue was purified by preparative TLC (silica gel, 6:4 hexane:EtOAc) to furnish 2'-O-(t-butyldimethylsilyl)-7-O-trifluoromethanesulfonylpaclitaxel (187.0 mg, 92% yield). $^1H$ NMR ($CDCl_3$, TMS, 400 MHz) d 8.12 (d, 2H), 7.73 (d, 2H), 7.60 (t, 1H), 7.53–7.30 (m, 10H), 7.09 (d, 1H, J=8.9, $H_{NH}$), 6.62 (s, 1H, $H_{10}$), 6.25 (t, 1H, J=9.2, $H_{13}$), 5.76 (q, 1H, J=8.9, 2.6, $H_3'$), 5.74 (d, 1H, J=7.0, $H_2$), 5.49 (dd, 1H, J=7.5, 10.1, $H_7$), 4.94 (d 1H, J=8.6, $H_5$), 4.67 (d, 1H, J=2.0, $H_2'$), 4.37 (d, 1H, J=8.5, $H_{20}$), 4.22 (d, 1H, J=8.5, $H_{20}$), 3.97 (d, 1H, J=7.0, $H_3$),2.85 (m,1H, $H_6$) 2.60 (s, 3H, —$CH_3$), 2.39 (m, 1H, $H_{14}$), 2.19 (s, 3H, —$CH_3$), 2.18 (m, 2 H, $H_6$, $H_{14}$), 2.08 (s, 3H, —$CH_3$), 1.89 (s, 3H, —$CH_3$), 1.22 (s, 3H, —$CH_3$), 1.18 (s, 3H, —$CH_3$), 0.8 (s, 9H), -0.02 (s, 3H), -0.29 (s, 3H). $^{13}C$ NMR ($CDCl_3$, TMS, 100 MHz) d 200.97, 171.89, 171.16, 169.34, 167,71, 167.42, 141.75, 138.77, 134.66, 134,45, 133.48, 132.46, 130.84, 129.52, 129.47, 129.40, 129.38, 128.65, 127.59, 127.00, 86.39, 83.68, 80.64, 79.25, 76.94, 75.77, 75.74, 74.92, 71.69, 57.97, 56.23, 47.55, 43.75, 36.32, 34.67, 26.76, 26.23, 26.13, 23.47, 22.01, 21.29, 18.75, 14.87, 14.80, 11.538, −4.54, −5.20. LRFABMS m/z calcd for $C_{54}H_{65}NO_{16}F_3SiS$ [MH]$^+$ 1100, found 1100.

2'-O-(triethylsilyl)-6,7-dehydropaclitaxel [3a]

The triflate 2a (17.6 g, 16 mmol) was dissolved in 75 mL of dry THF and then 12.18 g (80 mmol) of DBU was added. The reaction was heated at reflux for 2 hours and then diluted with ethyl acetate. The organic layer was washed five times with water and then brine, dried over anhydrous magnesium sulfate, filtered, and concentrated in vacuo. The crude product was dissolved in methylene chloride and then 16 mmol of imidazole and 8 mmol of triethylsilyl chloride were added. The reaction was stirred for 1.5 h at ambient temperature, diluted with ethyl acetate, washed with two portions of water, dried over anhydrous magnesium sulfate and concentrated in vacuo. The crude material was purified by flash chromatography over silica gel using 2:1 hexane/ethyl acetate as eluent to provide 15.0 g (99%) of the title compound.

2'-O-(t-butyldimethylsilyl)-6,7-dehydropaclitaxel [3b]

To a stirred solution of 2'-(t-butyldimethylsilyl)-7β-trifluoromethanesulfonylpaclitaxel [2b], (202.0 mg, 0.18 mmol) in dry dichloromethane (1.0 mL) was added 1,8-diazabicyclo (5,4,0) undec-7-ene (DBU, 300.0 mL, 2.0 mmol). The mixture was kept stirring at 40° C. for 4 hours. The reaction mixture then was diluted with ethyl acetate (2.0 ml) and washed with diluted HCl, diluted NaHCO$_3$ solution, water and brine. The aqueous layer was extracted with additional ethyl acetate (2×2 mL). The combined organic layers were dried over sodium sulfate and evaporated to give crude product. Purification of the crude product by preparative silica gel TLC (7:3 hexane:ethyl acetate) furnished two compounds: 2'-(t-butyldimethylsilyl)-6,7-dehydropaclitaxel [3b] (150.0 mg, 86%) and 6,7-dehydropaclitaxel (21.3 mg, 13.9%). Spectoscopic data for 3b: $^1$H-NMR (CDCl$_3$, TMS, 400 MHz) d 8.12 (d, 2H), 7.73 (d, 2H), 7.60 (t, 1H), 7.53–7.30 (m, 5H), 7.07 (d, 1H, J=8.9, H$_{NH}$), 6.24 (s, 1H, H$_{10}$), 6.25 (t, 1H, J=9.2, H$_{13}$), 6.08 (dd,1H, J=9.9, 5.6, H$_6$), 5.87 (d, 1H, J=9.9, H$_7$), 5.86 (d, 1H, J=6.5, H$_2$), 5.72 (d, 1H, J=8.6, H$_3$'), 5.12 (d 1H, J=5.5, H$_5$), 4.65 (d, 1H, J=2.0, H$_2$'), 4.45 (d, 1H, J=8.1, H$_{20}$), 4.34 (d, 1H, J=8.1, H$_{20}$), 4.03 (d, 1H, J=6.5, H$_3$), 2.58 (s, 3H, —CH$_3$), 2.44 (m, 1H, H$_{14}$), 2.22 (s, 3H, —CH$_3$), 2.18 (m, 2 H, H$_6$, H$_{14}$), 1.88 (s, 3H, —CH$_3$), 1.83 (s, 3H, —CH$_3$), 1.24 (s, 3H, —CH$_3$), 1.14 (s, 3H, —CH$_3$), 0.79 (s, 9H), −0.05 (s, 3H), −0.32 (s, 3H). $^{13}$C NMR (CDCl$_3$, TMS, 100 MHz) d 205.44, 171.32, 169.56, 169.39, 166.91, 166.87, 141.60, 140.03, 138.27, 134.06, 133.67, 133.61, 131.76, 130.19, 129.16, 128.80, 128.73, 128.71, 128.69, 127.92, 126.96, 126.36, 126.126, 81.22, 81.12, 76.31, 75.82, 75.64, 75.12, 71.23, 60.36, 55.65, 55.40, 35.98, 26.29, 25.49 23.14, 22.12, 22.02, 20.744, 20.46, 18.09, 14.62, 14.17, −5.28, −5.89. LRFABMS m/z calcd for $C_{53}H_{64}NO_{13}Si$ [MH]$^+$ 950, found 950.

2'-O-(triethylsilyl)-6α-hydroxy-7-epi-paclitaxel [4a]

The olefin 3a was dissolved in l80 mL of acetone and 22.5 mL of water. NMO (4.06 g, 34.74 mmol) was added and the reaction was stirred for 12 days. Silica gel was added and the reaction was concentrated in vacuo to provide a near free flowing powder which was placed on top of a flash chromatography silica gel column. Elution with 1:1 hexane/ethyl acetate provided 13.35 g (86%) of the desired diol.

2'-O-(t-Butyldimethylsilyl)-6α-hydroxy-7-epi-paclitaxel [4b]

To a solution of 2'-O-(t-butyldimethylsilyl)-6,7-dehydropaclitaxel [3b], (60.0 mg, 0.063 mmol) in THF (500 mL, 10 drops H$_2$O) were added osmium tetraoxide (2.5 wt. 2.5% solution in 2-methyl-2-propanol, 150 mL, 0.015 mmol) and 4-methyl morpholine-N-oxide (NMO, 50 mg, 0.42 mmol). The mixture was kept stirring at room temperature for 4 hours. Additional osmium tetraoxide solution (150 mL, 0.015 mmol) was then added to the reaction mixture to accelerate the reaction. The reaction mixture was kept stirring at room temperature for additional 5 hours. To the reaction solution was added sodium bisulfite (25 mg) and the mixture was stirred for 10 minutes, then diluted with EtOAc (1 mL), filtered through Celite, and washed with H$_2$O and brine. The aqueous layer was extracted with additional EtOAc (2×2 mL). The combined organic layers were dried over Na$_2$SO$_4$ and evaporated. Isolation of the residue on preparative TLC plate (silica gel, 1:1 hexane:EtOAc) furnished starting material (7.2 mg, 12%) and a more polar compound 2'-O-(t-butyldimethylsilyl)-6a-hydroxy-7-epi-paclitaxel [4b] (48.0 mg, 78% yield). $^1$H NMR (CDCl$_3$, TMS, 400 MHz) d 8.15 (d, 2H), 7.70 (d, 2H), 7.64– 7.26 (m, 6H), 7.07 (d, 1H, J=8.8, H$_{NH}$), 6.83 (s, 1H, H$_{10}$), 6.29 (t, 1H, J=8.8, H$_{13}$), 5.79 (q, 1H, J=8.8, 2.4, H$_3$'), 5.74 (d, 1H, J=7.6, H$_2$), 4.71 (d, 1H, J=12.0, H$_{7\text{-}OH}$), 4.68 (d, 1H, J=2.0, H$_5$), 4.66 (bs, 2H, H$_{20}$), 4.36 (s, 1H, H$_2$'), 4.18 (m, 1H, H$_6$), 3.87 (d, 1H, J=7.6, H$_3$), 3.70 (q, 1H, J=5.2, 12.0, H$_7$), 2.90 (d, 1H, J=8.2, H$_{6\text{-}OH}$), 2.62 (s, 3H, —CH$_3$), 2.42–2.10 (m, 2H, H$_{14}$), 2.18 (s, 3H, —CH$_3$), 1.90 (s, 3H, —CH$_3$), 1.62 (s, 3H, —CH$_3$), 1.18 (s, 3H, —CH$_3$), 1.12 (s, 3H, —CH$_3$), 0.78 (s, 9H), −0.03 (s, 3H), −0.3 (s, 3H). HRFABMS m/z calcd for $C_{47}H_{52}NO_{15}$ [MH]$^+$ 870.3337, found 870.3336.

Preparation of Starting Materials—Scheme III

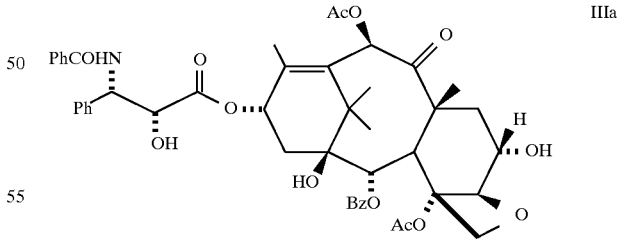

IIIa

The diol 4a (1.773 g, 1.809 mmol), thiocarbonyldiimidazole (0.996 g, 5.427 mmol), DMAP (0.618 g, 5.065 mmol) were dissolved in 50 mL THF and allowed to stir overnight. The reaction was diluted with EtOAc, washed with NaHCO$_3$, and brine. The solution was dried over MgSO$_4$, filtered, and concentrated. The residue was chromatographed over silica gel (1:1 hexane/ethyl acetate) to yield 1.646 g of product 5a (89%).

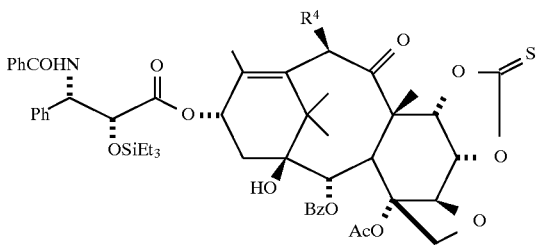

5a

ESILRMS M+NH$_4^+$ calcd. for C$_{54}$H$_{63}$O$_{15}$N$_2$S Si: 1043. Found: 1043.

Anal. calcd. for C$_{54}$H$_{63}$O$_{15}$N S Si: C, 63.20; H, 6.19; N, 1.36. Found: C, 63.04; H, 6.22; N, 1.33.

IR(KBr) 3438(br.), 2958, 1746, 1717, 1282, 1236 cm$^{-1}$.

$^1$H NMR (CDCl$_3$, 300 MHz) d 8.15(d, J=7.2 Hz, 2H), 7.74(d, J=7.2 Hz, 2H), 7.63–7.32(m, 11H), 7.12(d, J=9.0 Hz, 1H), 6.87(s, 1H), 6.25(br. t., 1H), 5.83(d, J=6.9Hz, 1H), 5.70(d, J=9.0, 1H), 4.97(d, J=11.4 Hz, 1H), 4.87(s, 1H), 4.72(m, 2H), 4.39(d, J=8.1 Hz, 1H), 4.22(d, J=8.1 Hz, 1H), 4.00(D, J=6.9 Hz, 1H), 2.57(s, 3H), 2.43–2.35(m, 1H), 2.21(s, 3H), 2.16–2.08(m, 1H), 2.03(m, 4H), 1.87(s, 3H), 1.21(s, 3H), 1.17(s, 3H), 0.79(m, 9H), 0.44(m, 6H).

The thiocarbonate 5a (0.200 g, 0.196 mmol), AIBN(cat.), (aza-isobutyrylnitrile (catalytic)) and Bu$_3$GeH (0.479 g, 1.96 mmol) were dissolved in 3 mL toluene under Argon. The reaction mixture was frozen, dried in vacuo, and thawed three times to remove O$_2$. The reaction was heated to 85° C. for 1 hr. The reaction mixture was concentrated and chromatographed over silica gel (1.5:1 hexane/ethyl acetate) to yield 0.137 g of product 6a (72%).

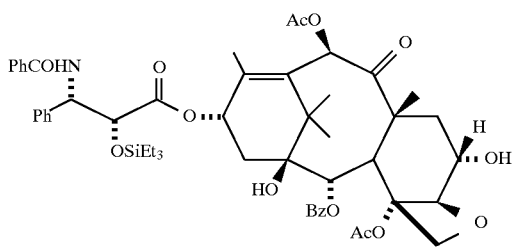

6a

ESILRMS M+H calcd for C$_{53}$H$_{65}$O$_{14}$N Si: 968. Found: 968.

Anal. calcd. for C$_{53}$H$_{65}$O$_{14}$NSi—H$_2$O: C, 64.55; H, 6.85; H, 1.42. Found: C, 64.49; H, 6.82; N, 1.41.

IR(KBr) 3442(br.), 2956, 1734, 1486, 1372, 1244, 710 cm$^{-1}$.

$^1$H NMR (CDCl$_3$, 300 MHz) d 8.13(d, J=8.7 Hz, 2H), 7.72(d, J=8.4 Hz, 2H), 7.62–7.33(m, 11H), 7.10(d, J=8.7 Hz, 1H), 6.45(s, 1H), 6.24(t, J=8.7 Hz, 1H), 5.71–5.64(m, 2H), 4.80(s, 1H), 4.66(d, J=2.1 Hz, 1H), 4.31(d, J=8.4 Hz, 1H), 4.18–4.14(m, 2H), 3.78(d, J=7.5 Hz, 1H), 2.54(s, 3H), 2.48–2.39(m, 1H), 2.20(s, 3H), 2.17–2.08(m, 1H), 2.02(d, J=9.0 Hz, 2H), 1.90(s,4H), 1.77(s,1H), 1.71(s, 3H), 1.19(s, 3H), 1.10(s, 3H), 0.79(m, 9H), 0.41(m,6H).

To a solution of the 6-alpha alcohol 6a (7.63 g, 7.89 mmol) in acetonitrile at 0° C. was added 1N HCl (15.78 mL, 15.78 mmol) and the solution stirred for 1 hr. The solution was diluted with ethyl acetate, washed with saturated bicarbonate and brine, dried over MgSO$_4$, and concentrated. The residue was chromatographed over silica gel (2:1 hexane/ethyl acetate) to give 6.07 g of diol VIa (90%)

ESIHRMS M+H calcd for C$_{47}$H$_{52}$NO$_{14}$ 854.3388 Found: 854.3377.

IR(KBr) 3436(br.), 2985, 1732, 1648, 1244 cm$^{-1}$.

$^1$H NMR (CDCl$_3$, 300 MHz) d 8.13(d, J=6.9 Hz, 2H), 7.70(d, J=6.9 Hz, 2H), 7.60–7.26(m, 11H), 6.94(d, J=9.0, 1H), 6.41(s, 1H), 6.20(br. t., 1H), 5.77(d, J=6.3 Hz, 1H), 5.64(d, J=7.5 Hz, 1H), 4.77(s, 2H), 4.28(d, J=8.4 Hz, 1H), 4.16–4.08(m, 2H), 3.76(d, J=7.2 Hz, 1H), 3.48(s, 1H), 2.40–2.36(m, 4H), 2.28–2.19(m, 4H), 2.01–1.80(m, 4H), 1.80 (s, 3H), 1.70(s, 3H), 1.19(s, 3H), 1.10(s, 3H).

$^{13}$C NMR (Acetone, 300 MHz) d 173.5, 170.9, 169.7, 166.5, 141.6, 140.3, 135.5, 134.5, 134.0, 132.1, 131.2, 130.8, 129.4, 129.2, 129.1, 128.3, 128.19, 128.15, 93.7, 85.1, 78.8, 77.3, 76.4, 74.7, 74.6, 71.6, 71.5, 56.8, 53.7, 45.0, 44.3, 43.7, 37.1, 30.5, 28.9, 28.8, 26.6, 23.0, 22.2, 20.6, 16.3, 14.5.

Alternate Deoxygenation Procedure

To a solution of the thiocarbonate 5a (0.201 g, 0.197 mmol) in toluene (6.4 mL) was added Bu$_3$SnH (0.530 ml, 1.97 mmol) and AIBN (cat.). The reaction mixture was refluxed for 15 min., cooled, and concentrated. The residue was chromatographed over silica gel (1:1 hexane/ethyl acetate) to give 120 mg of a mixture of two products (63%). To a solution of the deoxygenation products (0.373 g, 0.386 mmol) in CH$_3$CN (5 mL) at 0° C. was added 1N HCl (0.771 mL, 0.771 mmol). The reaction was stirred at 0° C. for 50 min., diluted with EtOAc, washed with NaHCO$_3$, and brine. The solution was dried over MgSO$_4$, concentrated and the residue chromatographed over silica gel (1:2 hexane/ethyl acetate) to give the desired diol VIa 176 mg along with 54 mg of the C-10 desacetyl derivative VIb.

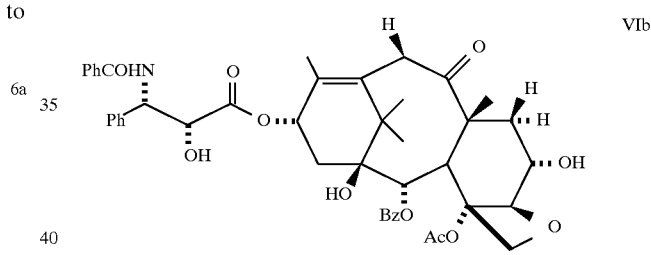

VIb

C-10 desacetyl diol [VIb]:

ESIHRMS M+H calcd. for C$_{45}$H$_{50}$NO$_{12}$ 796.3333. Found: 796.3361.

IR(KBr) 3436(br.), 1728, 1648, 1272, 1108 cm$^{-1}$.

$^1$H NMR (CDCl$_3$, 300 MHz) 8.13(d, J=8.4 Hz, 2H), 7.72(d, J=8.4 Hz, 2H), 7.63–7.30(m, 11H), 6.96(d, J=8.7 Hz, 1H), 6.11(t, J=9.0, 1H), 5.78(d, J=9.0 Hz, 1H), 5.65(d, J=7.5 Hz, 1H), 4.77–4.73(m, 2H), 4.28(d, J=7.8 Hz, 1H), 4.16–4.06(m, 2H), 3.96(d, J=6.6 Hz, 1H), 3.80(d, J=16.5 Hz, 2H), 3.47–3.31(m, 3H), 2.44–2.36(m, 4H), 2.27–2.20(m, 1H), 1.95(d, J=9.0 Hz, 2H), 1.68(s, 3H), 1.66(s, 3H), 1.15(s, 3H), 1.08(s, 3H).

Preparation of Starting Materials—Scheme IV

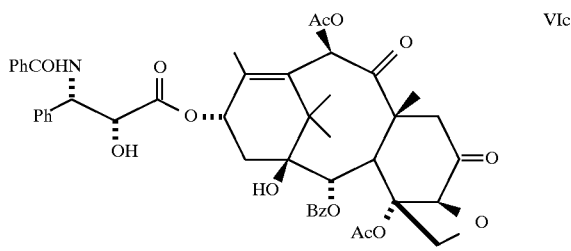

VIc

A solution of the alcohol 6a (0.193 g, 0.2 mmol) and NMO (0.049 g, 0.419 mmol) in CH$_2$Cl$_2$ (3 mL) was stirred over 4 Å molecular sieves for 10 min. before TPAP (10 mole %) was added as a solid. The reaction was stirred for 15 hrs. The solution was filtered through celite, concentrated, diluted with EtOAc, washed with Na₂SO₃, and brine. The solution was dried over MgSO₄, filtered, and concentrated. The residue was chromatographed over silica gel (1:1 hexane/ethyl acetate) to give 0.145 g of ketone 11a (75%).

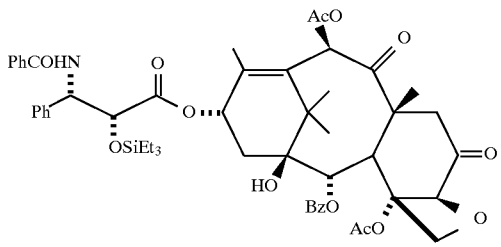

ESILRMS M+H calcd for $C_{53}H_{64}O_{14}N$ Si: 966. Found: 966.

Anal. calcd. for $C_{53}H_{63}O_{14}N$ Si—$H_2O$: C, 64.48; H, 6.65; N, 1.42. Found: C, 64.73; H, 6.54; N, 1.36.

IR(KBr) 3442(br.), 2956, 1730, 1666, 1484, 1372, 1242 cm⁻¹.

¹H NMR (CDCl₃, 300 MHz) d 8.14(d, J=6.9 Hz, 2H), 7.71(d, J=8.7 Hz, 2H), 7.60–7.31(m, 11H), 7.09(d, J=9.0 Hz, 1H), 6.42(s, 1H), 6.27(br. t., 1H), 5.74–5.69(m, 2H), 4.82(s, 1H), 4.68(d, J=2.1 Hz, 1H), 4.39( dd, J=19.5, 8.7 Hz, 2H), 4.13(d, J=7.5 Hz, 1H), 3.15(d, J=14.1 Hz, 1H), 2.59(s, 3H), 2.51– 2.42(m, 1H), 2.31(d, J=13.8 Hz, 1H), 2.20(s, 3H), 2.19–2.10(m, 1H), 1.91(s, 3H), 1.72(s, 1H), 1.67(s, 3H), 1.22(s, 3H), 1.11(s, 3H), 0.79(m, 9H), 0.42(m, 6H).

A solution of the silyl ketone 11a (0.051 g, 0.053 mmol) in CH₃CN was cooled to 0° C. and HCl (1N, 0.106 mL, 0.106 mmol) was added. The reaction was stirred at 0° C. for 1 hr. The reaction was diluted with EtOAc, washed with NaHCO₃, and brine. The solution was dried over MgSO₄, filtered, and concentrated. The residue was chromatographed over silica gel (1:1 hexane/ethyl acetate) and recrystallized from ethyl acetate/hexane to yield 0.041 g of the title compound, ketone VIc (80%).

ESIHRMS (M+Na calcd. for $C_{47}H_{49}O_{14}N$ Na: 874.3051. Found: 874.3014.

IR(KBr) 3448(br.), 2955, 1732, 1654, 1374, 1242 cm⁻¹.

¹H NMR (CDCl₃, 300 MHz) d 8.15(d, J=6.0 Hz, 2H), 7.70(d, J=6.9 Hz, 2H), 7.64–7.34(m, 11H), 6.90(d, J=9.3 Hz, 1H), 6.39(s, 1H), 6.25(t, J=8.4 Hz, 1H), 5.80(d, J=9.0, 1H), 5.70(d, J=7.5, 1H), 4.79(s, 2H), 4.42(d, J=8.4 Hz, 1H), 4.35(d, J=8.4 Hz, 1H), 4.11(d, J=7.5 Hz, 1H), 3.47(d, J=5.4 Hz, 1H), 3.11(d, J=13.8 Hz, 1H), 2.50–2.42(m, 4H), 2.33–2.25(m, 3H), 2.20(s, 3H), 1.84(s, 4H), 1.66(s, 3H), 1.22(s, 3H), 1.12(s, 3H).

¹³C NMR (CDCl₃, 75.5 MHz) d 202.4, 202.1, 172.9, 170.9, 169.6, 167.3, 166.8, 141.0, 137.9, 133.9, 133.6, 133.3, 132.0, 130.3, 129.1, 129.0, 128.9, 128.7, 128.4, 127.1, 127.0, 85.0, 84.4, 78.7, 78.2, 76.6, 75.2, 73.7, 73.1, 72.2, 55.0, 53.0, 51.0, 45.2, 43.0, 36.1, 26.2, 22.6, 21.6, 20.7, 16.3, 14.5.

Preparation of Starting Materials—Scheme V

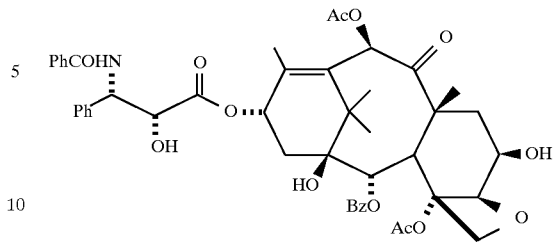

The ketone 11a (0.084 g, 0.087 mmol) was dissolved in 3 mL of EtOH and cooled to 0° C. NaBH₄ (0.003 g, 0.087 mmol) was added as a solid and the reaction was stirred at 0° C. for 1 hr. The reaction was quenched with H₂O, diluted with ethyl acetate and washed with brine. The solution was dried over MgSO₄ and concentrated. The residue was chromatographed over silica gel (1:1 hexane/ethyl acetate) to give 0.0693 g of 6-beta alcohol 12a (82%).

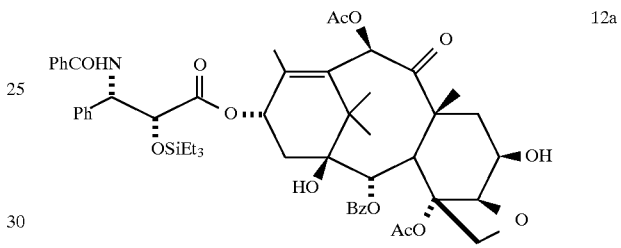

ESILRMS M–H calcd. for $C_{53}H_{64}O_{14}N$ Si: 966. Found: 966

IR(KBr) 3442(br.), 2956, 1732, 1664, 1485, 1372, 1242 cm⁻¹.

¹H NMR (CDCl₃, 300 MHz) d 8.14(d, J=7.2 Hz, 2H), 7.71(d, J=76.9 Hz, H), 7.54–7.29(m, 11H), 7.07(d, J=7.1 Hz, 1H), 6.44(s, 1H), 6.24(br. t., 1H), 5.69(d, J=7.8 Hz, 1H), 4.97(d, J=8.4 Hz, 1H), 4.65(s, 1H), 4.46(d, J=8.1 Hz, 1H), 4.24(m, 2H), 3.65(d, J=6.9 Hz, 1H), 2.75(br. d., 1H), 2.53(s, 3H), 2.45–2.35(m, 1H), 2.22–2.10(m, 5H), 1.86(s, 3H), 1.77(s, 3H), 1.19(s, 3H), 1.10(s, 3H), 0.78(m, 9H), 0.41(m, 6H).

The silyl ether 12a (0.063 mg, 0.065 mmol) was dissolved in 5 mL of CH₃CN and cooled to 0° C. and HCl (1N, 0.130 mL, 0.130 mmol) was added and the reaction was stirred for 1 hr. The reaction was diluted with ethyl acetate and washed with NaHCO₃, brine. The solution was dried over MgSO₄, filtered, and concentrated. The residue was chromatographed over silica gel (1:2 hexane/ethyl acetate) to give 0.053 g of the title compound, diol VId (95%).

ESILRMS M–H calcd for $C_{47}H_{50}O_{14}N$:852. Found: 852.

Anal. calcd. for $C_{47}H_{51}O_{14}N$: C, 66.11; H, 6.02; N, 1.64. Found: C, 65.92; H, 6.14; N, 1.54.

IR(KBr) 3442(br.), 2945, 1732, 1648, 1372, 1242 cm⁻¹.

¹H NMR (CDCl₃, 300 MHz) d 8.14(d, J=6.9, 2H), 7.71(d, J=7.2 Hz, 2H), 7.61–7.25(m, 11H), 6.93(d, J=9.0 Hz, 1H), 6.41(s, 1H), 6.19(br. t., 1H), 5.78(d, J=6.3 Hz, 1H), 5.68(d, J=7.2Hz, 1H), 4.95(d, J=8.4 Hz, 1H), 4.78(m, 1H), 4.46(d, J=8.4 Hz, 1H), 4.22(m,2H), 3.66(d, J=6.9 Hz, 1H), 3.47(d, J=5.4 Hz, 1H), 2.72(br. d., 1H), 2.39(s, 3H), 2.35–2.24(m, 2H), 2.19(s, 3H), 2.18–2.11(m,1H), 1.85–1.76(m, 2H), 1.78 (s, 3H), 1.56 (s,3H), 1.18(s, 3H), 1.10(s, 3H).

Preparation of Starting Materials—Scheme VI

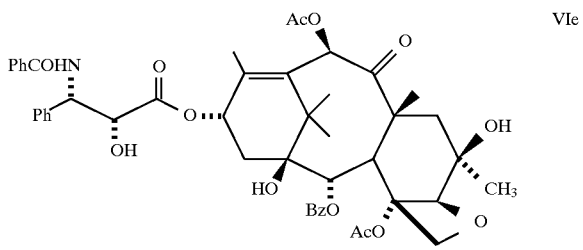

A solution of the silyl ketone 11a (0.100 g, 0.104 mmol) was dissolved in $CH_2Cl_2$, cooled to −20° C., and Me3Al (2.0M in hexane, 0.415 mL, 0.830 mmol) was added via syringe. The reaction was stirred at −15° to −20° C. for 30 min. The reaction was quenched with $H_2O$, diluted with EtOAc, washed with brine. The solution was dried over $MgSO_4$, filtered, and concentrated. The residue was chromatographed over silica gel (1:1 hexane/ethyl acetate) to yield 0.090 g of tertiary alcohol 13a (88%).

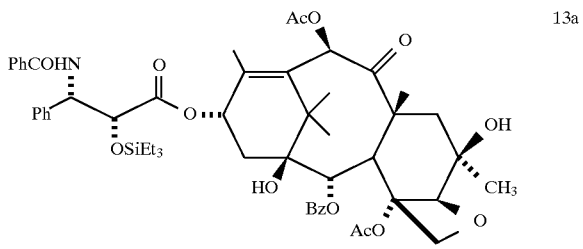

ESILRMS $M+NH_4^+$ calcd for $C_{54}H_{71}O_{14}N_2Si$: 999. Found: 999.

Anal. calcd. for $C_{54}H_{67}O_{14}NSi—H_2O$: C, 64.84; H, 6.95; N, 1.40. Found: C, 64.56; H, 6.86; N, 1.21.

IR(KBr) 3444(br.), 2956, 1734, 1244, 710 cm$^{-1}$.

$^1H$ NMR ($CDCl_3$, 300MHz) d 8.14(d, J=6.9 Hz, 2H), 7.71(d, J=6.9 Hz, 2H), 7.60–7.31(m, 11H), 7.08(d, J=9.0 Hz, 1H), 6.42(s, 1H), 6.24(br. t., 1H), 5.73–5.64(m, 2H), 4.67(d, J=2.1 Hz, 1H), 4.57(s, 1H), 4.43(d, J=8.1 Hz, 1H), 4.30(d, J=8.7 Hz, 1H), 3.73(d, J=6.9 Hz, 1H), 3.22(s, 1H), 2.55(s, 3H), 2.43–2.35(m, 1H), 2.19(s, 3H), 2.14–2.06(m, 1H), 1.98–1.81 (m, 2H), 1.88(s, 3H), 1.75(s, 3H), 1.27(s, 3H), 1.19(s, 3H), 1.09(s, 3H), 0.78(m, 9H), 0.44(m, 6H).

The 2' protected tertiary alcohol 13a (0.077 g, 0.078 mmol) was dissolved in 3 mL of THF and was shaken with $Bu_4NF$ (0.086 mL, 1.0M in THF, 0.086 mmol) diluted with ethyl acetate and washed with $H_2O$, brine. The solution was dried over $MgSO_4$, filtered, and concentrated. The residue was chromatographed over silica gel (1:1 hexane/ethyl acetate) to give 0.0572 g of tertiary alcohol VIe (85%).

ESIHRMS M+Na calcd for $C_{48}H_{53}O_{14}N$ Na: 890.3364. Found: 890.3389.

IR(KBr) 3442(br.), 1736, 1648, 1372, 1242 cm$^{-1}$.

$^1H$ NMR ($CDCl_3$, 300MHz) d 8.14(d, J=7.2 Hz, 2H), 7.71(d, J=7.2 Hz, 2H), 7.61–7.33(m, 11H), 6.94(d, J=9.0 Hz, 1H), 6.39(s, 1H), 6.19(br. t., 1H), 5.78(d, J=8.7 Hz, 1H), 5.68(d, J=6.9 Hz, 1H), 4.77(m, 1H), 4.55(s, 1H), 4.42(d, J=8.4 Hz, 1H), 4.28(d, J=8.4 Hz, 1H), 3.71(d, J=6.9 Hz, 1 H), 3.44(d, J=5.1 Hz, H), 3.19(s, 1H), 2.41(s, 3H), 2.35–2.25 (m, 2H), 2.20(s, 3H), 1.81–1.74(m, 2H), 1.77 (s, 3H), 1.74 (s, 3H),1.25(s, 3H), 1.18(s, 3H), 1.10(s, 3H).

$^{13}C$ NMR ($CDCl_3$, 75.5 Hz) d 205.0, 172.6, 170.1, 166.9, 140.0, 137.8, 133.6, 131.9, 130.1, 129.1, 128.9, 128.7, 128.6, 128.2, 126.9, 126.8, 89.9, 81.7, 78.8, 75.4, 73.7, 73.0, 72.1, 68.2, 54.8, 53.5, 48.6, 44.5, 42.7, 35.8, 31.3, 26.1, 22.5, 21.3, 20.7, 16.2, 14.3.

Preparation of Starting Materials—Scheme VIg

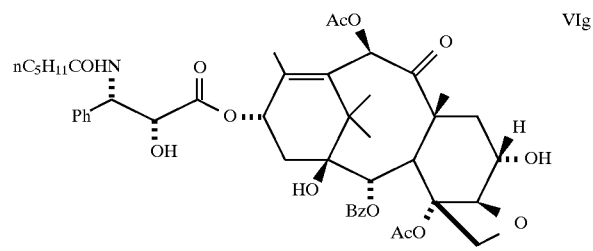

A solution of diol 6a (6.07 g, 7.10 mmol) in methylene chloride was treated with tetrabutylammonium borohydride (3.02 g, 11.73 mmol) at ambient temperature for 60 hours. Acetic acid (25.66 mL) was added slowly to the reaction mixture and the solution concentrated. The residue was chromatographed over silica (4:1 hexane/ethyl acetate) to give 3.27 g of baccatin derivative IV-z.

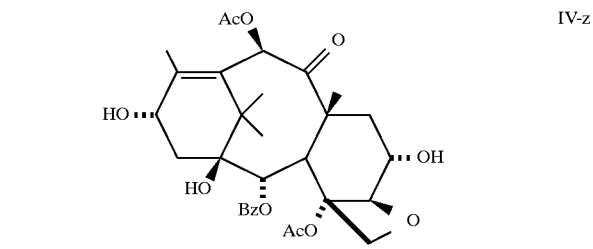

The baccatin derivative IV-z (3.27 g, 5.58 mmol) was dissolved in DMF with imidazole (1.18 g, 17.30 mmol). TESCl (2.81 mL, 16.74 mmol) was added and the reaction was stirred for 1 hr. The reaction was diluted with EtOAc, and washed with $H_2O$ then brine. The solution was dried over $MgSO_4$, filtered, and concentrated. The residue was chromatographed over silica gel (2:1 hexane/ethyl acetate) to give 2.592 g (52%) of the monosilylated baccatin IV-y.

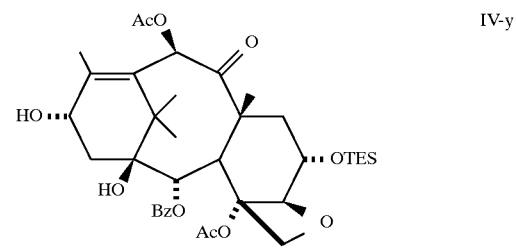

ESILRMS M-H calcd. for $C_{37}H_{51}O_{11}Si$: 699. Found: 699.

IR(KBr) 3528(br.), 2956, 1714, 1454, 1372, 1230 cm$^{-1}$

The monosilyl baccatin derivative IV-y (1.400 g, 2.00 mmol) was dissolved in THF and cooled to −78° C. n-BuLi (1.0 mL, 2.5M in hexanes, 2.5 mmol) was added and the reaction was stirred at −78° C. for 15 min. Lactam 16b (3R, 4S)-N-hexanoyl-4-phenyl-3-triethylsilyoxyazetidin-2-one (3.00 g, 8.00 mmol) was added as a solution in THF. The reaction was warmed to 0° C., stirred at 0° C. for 50 min., diluted with EtOAc, washed with $NH_4Cl$, and then brine. The solution was dried over $MgSO_4$, filtered, and concentrated in vacuo. The residue was chromatographed over silica gel (20% ethyl acetate/hexane) to give 1.615 g of bis silyl ether 9d (75%).

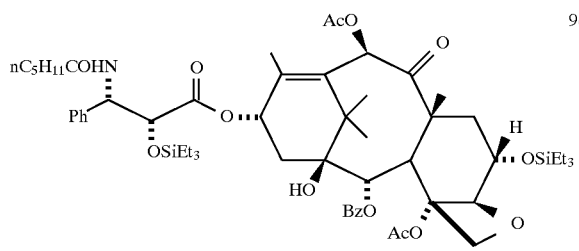

9d

ESILRMS M−H calcd. for $C_{58}H_{84}O_{14}N\ Si_2$: 1074. Found: 1074.

IR(KBr) 3440(br.), 2958, 1736, 1682, 1496, 1372, 1244 cm$^{-1}$.

Anal. calcd. for $C_{58}\ H_{85}\ O14\ N\ Si2$: C, 64.71; H, 7.96; N, 1.30. Found: C, 64.48; H, 7.97; N, 1.30.

The bis silyl ether 9d (1.652 g, 1.54 mmol) was dissolved in CH$_3$CN and cooled to 0° C. HCl (3.18 mL, 1.0N, 3.18 mmol) was added and the reaction was stirred at 0° C. for 75 min., diluted with EtOAc, washed with NaHCO$_3$, and then brine. The solution was dried over MgSO$_4$, filtered, and concentrated. The residue was chromatographed over silica gel (60% ethyl acetate/hexane) to give 1.144 g (87%) of diol VIg.

ESILRMS M+H calcd. for $C_{46}H_{58}O_{14}N$: 848. Found: 848.

IR(KBr) 3420(br.), 2956, 1726, 1636, 1452, 1372, 1246 cm$^{-1}$.

Anal. calcd. for C46 H57 O14 N: C, 65.16; H, 6.78; N, 1.65. Found: C, 64.82; H, 6.71; N, 1.54.

Preparation of Starting Materials—Scheme VII

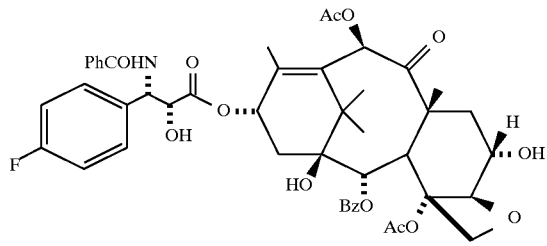

IIIh

The monosilyl baccatin derivative IV-y (0.800 g, 1.14 mmol) was dissolved in THF and cooled to −78° C. n-BuLi (0.571 mL, 2.5M in hexanes, 1.428 mmol) was added and the reaction was stirred at −78° C. for 15 min. Lactam 16c (±)-cis-N-benzoyl-4-(4-fluorophenyl)-3-triethylsilyoxyazetidin-2-one (2.42 g, 6.065 mmol) was added as a solution in THF. The reaction was stirred at −78° C. for 30 min. and at 0° C. for 30 min. The reaction was diluted with EtOAc, washed with NH$_4$Cl, and then brine. The solution was dried over MgSO$_4$, filtered, and concentrated. The residue was chromatographed over silica gel (20% ethyl acetate/hexane) to give 1.094 g of bis silyl ether 9e (75%).

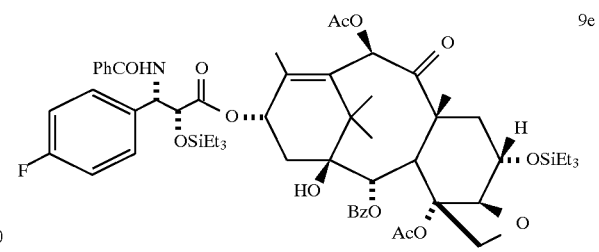

9e

ESILRMS M+H calcd. for $C_{59}H_{79}O_{14}N\ Si_2F$: 1100. Found: 1100.

IR(KBr) 3444(br.), 2956, 1736, 1671, 1482, 1370, 1232 cm$^{-1}$.

Anal. calcd. for $C_{59}\ H_{78}O_{14}\ N\ Si_2F$: C, 64.40; H, 7.14; N, 1.27. Found: C, 64.14; H, 6.95; N, 1.31.

The bis silyl ether 9e (0.419 g, 0.381 mmol) was dissolved in CH$_3$CN and cooled to 0° C. HCl (0.152 mL, 1.0N, 0.152 mmol) was added and the reaction was stirred at 0° C. for 1 hr. Diluted with EtOAc, washed with NaHCO$_3$, brine. The solution was dried over MgSO$_4$, filtered, and concentrated. The residue was chromatographed over silica gel (2:1 ethyl acetate/hexane) to give 0.289 g (72%) of diol VIh and approximately 15% of the other sidechain diastereomer.

ESILRMS M−H calcd. for $C_{47}H_{49}O_{14}N\ F$: 870. Found: 870.

IR(KBr) 3427(br.), 2948, 1729, 1652, 1511, 1371, 1237 cm$^{-1}$.

Anal. calcd. for $C_{47}\ H_{50}\ O_{14}\ N\ F$: C, 64.74; H, 5.78; N, 1.61. Found: C, 64.52; H, 5.95; N, 1.53.

Preparation of Starting Materials—Scheme IX, IV

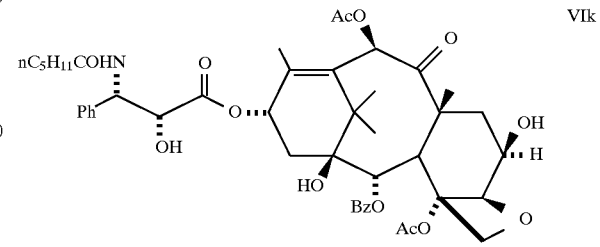

VIk

Bis silyl ether 9d (0.917 g, 0.853 mmol) was dissolved in MeOH and cooled to 0° C. A catalytic amount of Dowex H$^+$ resin was added and the reaction was stirred at 0° C. for 3 hr. The reaction was filtered, and concentrated. The residue was chromatographed over silica gel (1.5:1 hexane/EtOAc) to give 0.729 g of monodeprotected alcohol 6b (89%).

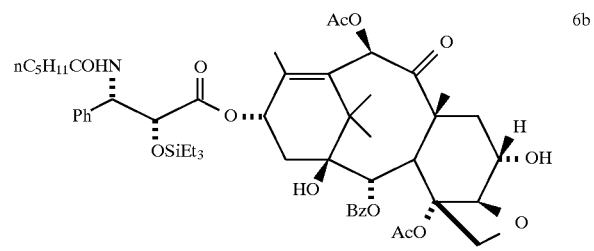

6b

ESILRMS M+H calcd. for $C_{52}H_{72}O_{14}N\ Si$: 962. Found: 962.

IR(KBr) 3438(br.), 2956, 1733, 1496, 1371, 1243 cm$^{-1}$.

Anal. calcd. for $C_{52}\ H_{71}\ O_{14}\ N\ Si$: C, 64.91; H, 7.44; N, 1.46. Found: C, 64.76; H, 7.33; N, 1.50.

The monosilyl alcohol 6b (0.720 g, 0.749 mmol) and NMO (0.184 g, 1.573 mmol) were dissolved in CH$_2$Cl$_2$ and stirred over 4 Å molecular sieves for 15 min. before TPAP (0.026 g, 0.075 mmol) was added. The reaction was stirred for 1 hr. The reaction was filtered through celite and concentrated. The residue was dissolved in EtOAc, washed with Na$_2$S$_2$O$_3$, brine. The solution was dried over MgSO$_4$, filtered and concentrated. The residue was chromatographed over silica gel (2:1 hexane/EtOAc) to give 0.648 g of silyl ketone 11b (90%).

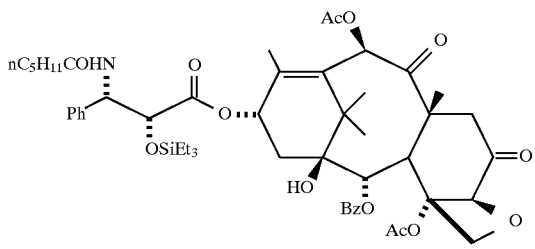

11b

ESILRMS M+H calcd. for $C_{52}H_{70}O_{14}N$ Si: 960. Found: 960.

IR(film) 3437(br.), 2956, 1729, 1676, 1241, 752, 709 cm$^{-1}$.

Anal. calcd. for $C_{52}$ $H_{69}$ $O_{14}$ N Si: C, 65.05; H, 7.24; N, 1.46. Found: C, 64.83; H, 7.23; N, 1.49.

Silyl ketone 11b (0.300 g, 0.313 mmol) was dissolved in EtOH and cooled to 0° C. before NaBH$_4$ (0.012 g, 0.313 mmol) was added as a solid. The reaction was stirred at 0° C. for 1 hr. The reaction was diluted with EtOAc, washed with H$_2$O, brine. The solution was dried over MgSO$_4$, filtered, and concentrated. The residue was chromatographed over silica gel (2:1 hexane/EtOAc). The residue was dissolved in CH$_3$CN and cooled to 0° C. HCl (0.626 mL, 1N, 0.626 mmol) was added and the reaction was stirred at 0° C. for 1 hr. The reaction was diluted with EtOAc, washed NaHCO$_3$, brine. The solution was dried over MgSO$_4$, filtered, and concentrated. The residue was chromatographed over silica gel (1:2 hexane/EtOAc) to give 0.216 g of diol VIk (82%).

ESILRMS M-H calcd. for $C_{46}H_{56}O_{14}N$: 846. Found: 846.

IR(KBr) 3440(br.), 2931, 1735, 1637, 1452, 1371, 1239 cm$^{-1}$.

Anal. calcd. for $C_{46}$ $H_{57}$ $O_{14}$ N: C, 65.16; H, 6.78; N, 1.65. Found: C, 64.86; H, 6.72; N, 1.56.

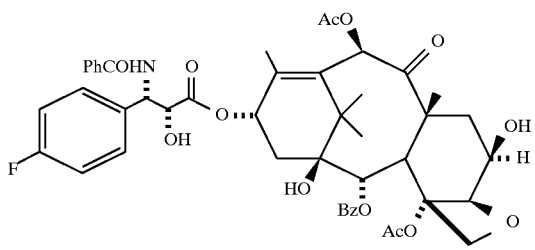

VII

Bis silyl ether 9e (0.575 g, 0.523 mmol) was dissolved in MeOH and cooled to 0° C. A catalytic amount of Dowex H$^+$ resin was added and the reaction was stirred at 0° C. for 3 hr. The reaction was filtered, and concentrated. The residue was chromatographed over silica gel (2:1 hexane/EtOAc) to give 0.313 g of monosilyl ether 6c (61%).

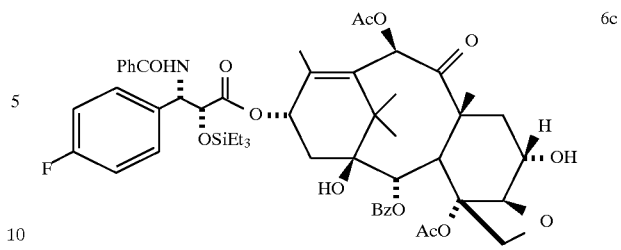

6c

ESILRMS M+H calcd. for $C_{53}H_{65}O_{14}N$ Si F: 986. Found: 986.

IR(KBr) 3439(br.), 2955, 1732, 1510, 1483, 1371, 1235 cm$^{-1}$.

Anal. calcd. for $C_{53}$ $H_{64}$ $O_{14}$ N Si F: C, 64.55; H, 6.54; N, 1.42. Found: C, 64.54; H, 6.46; N, 1.49.

The monosilyl alcohol 6c (0.305 g, 0.309 mmol) and NMO (0.076 g, 0.649 mmol) were dissolved in CH$_2$Cl$_2$ and stirred over 4 Å molecular sieves for 10 min. before TPAP (0.011 g, 0.03 mmol) was added. The reaction was stirred for 1 hr. The reaction was filtered through celite and concentrated. The residue was dissolved in EtOAc, washed with Na$_2$S$_2$O$_3$, brine. The solution was dried over MgSO$_4$, filtered and concentrated. The residue was chromatographed over silica gel (2:1 hexane/EtOAc) to give 0.266 g of 11c (87%).

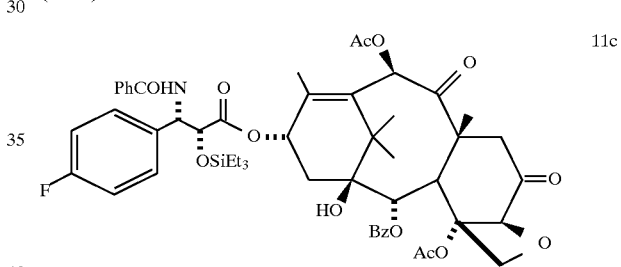

11c

ESILRMS M-H calcd. for $C_{53}H_{61}O_{14}N$ Si F: 982. Found: 982.

IR(film) 3439(br.), 2956, 1728, 1679, 1371, 1241 cm$^{-1}$.

Anal. calcd. for $C_{53}$ $H_{62}$ $O_{14}$ N Si F: C, 64.68; H, 6.35; N, 1.42. Found: C, 64.66; H, 7.08; N, 1.49.

The silyl ketone 11c (0.260 g, 0.264 mmol) was dissolved in EtOH and cooled to 0° C. before NaBH$_4$ (0.010 g, 0.264 mmol) was added as a solid. The reaction was stirred at 0° C. for 1 hr. The reaction was diluted with EtOAc, washed with H$_2$O, brine. The solution was dried over MgSO$_4$, filtered and concentrated. The residue was dissolved in CH$_3$CN and cooled to 0° C. HCl (0.528 mL, 1N, 0.528 mmol) was added and the reaction was stirred at 0° C. for 1 hr. The reaction was diluted with EtOAc, washed NaHCO$_3$, brine. The solution was dried over MgSO$_4$, filtered, and concentrated. The residue was chromatographed over silica gel (1:2 hexane/EtOAc) to give 0.182 g (79%) of diol VIl.

ESILRMS M-H calcd. for $C_{47}H_{49}O_{14}N$ F: 870. Found: 870.

IR(KBr) 3430(br.), 2944, 1731, 1652, 1510, 1485, 1371, 1238 cm$^{-1}$.

Anal. calcd. for $C_{47}$ $H_{50}$ $O_{14}$ N F: C, 64.74; H, 5.78; N, 1.61. Found: C, 64.44; H, 5.77; N, 1.55.

Preparation of Starting Materials—Scheme X

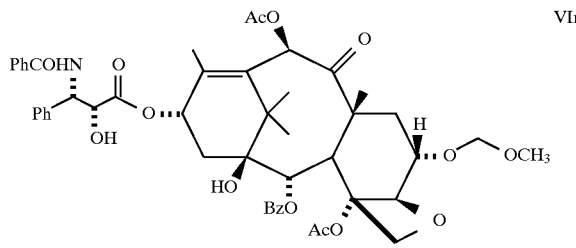

The alcohol 6a (0.513 g, 0.531 mmol) was dissolved in THF (10 mL) and cooled to −50° C. LiHMDS (0.637 mL, 1M in THF, 0.637 mmol) was added and the reaction was stirred at −50° C. for 15 min. MOMBr (0.052 mL, 0.637 mmol) was added and the reaction was allowed to warm to 0° C. over 30 min. and and stirred at 0° C. for 1 hr. The reaction was quenched with $H_2O$, and extracted with ethyl acetate. The solution was dried over $MgSO_4$, filtered, and concentrated. The residue was chromatographed over silica gel (1:1 hexane/ethyl acetate) to give 0.476 g of methoxymethyl ether 17a (89%).

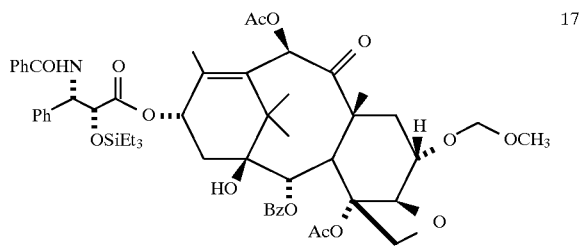

ESILRMS M+H calcd. for $C_{55}H_{70}O_{15}N$ Si: 1012. Found: 1012.

IR(KBr) 3442(br.), 2954, 1734, 1670, 1483, 1371, 1232 $cm^{-1}$.

Anal calcd. for $C_{55}H_{69}O_{15}$ N Si: C, 65.26; H, 6.87; N, 1.38. Found: C, 65.58; H, 6.88; N, 1.43.

The silyl ether 17a (0.446 g, 0.441 mmol) was dissolved in 15 mL of $CH_3CN$ and cooled to 0° C. HCl (0.882 mL, 1N, 0.882 mmol) was added and the reaction was stirred at 0° C. for 1 hr. The reaction was quenched with $NaHCO_3$(sat), and extracted with ethyl acetate. The solution was dried over $MgSO_4$, filtered, and concentrated. The residue was chromatographed over silica gel (1:2 hexane/ethyl acetate) to give 0.344 g of methoxymethyl ether VIm (87%).

ESILRMS M+H calcd. for $C_{49}H_{56}O_{15}N$: 898. Found: 898.

IR(KBr) 3428(br.), 2948, 1734, 1664, 1485, 1371, 1232 $cm^{-1}$.

Anal calcd. for $C_{49}H_{55}O_{15}$ N: C, 65.54; H, 6.17; N, 1.56. Found: C, 65.37; H,6.06; N, 1.37.

Preparation of Starting Materials—Scheme XI

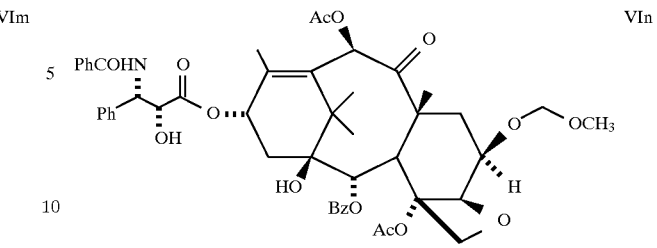

The alcohol 7a (0.472 g, 0.488 mmol) was dissolved in THF (6 mL) and cooled to −50° C. LiHMDS (0.586 mL, 1M in THF, 0.586 mmol) was added and the reaction was stirred at −50° C. for 15 min. MOMBr (0.048 mL, 0.586 mmol) was added and the reaction was allowed to warm to 0° C. over 30 min. and and stirred at 0° C. for 1 hr. The reaction was quenched with $H_2O$, and extracted with ethyl acetate. The solution was dried over $MgSO_4$, filtered, and concentrated. The residue was chromatographed over silica gel (1:1 hexane/ethyl acetate) to give 0.451 g of monosilyl methoxymethyl ether 18a (91%).

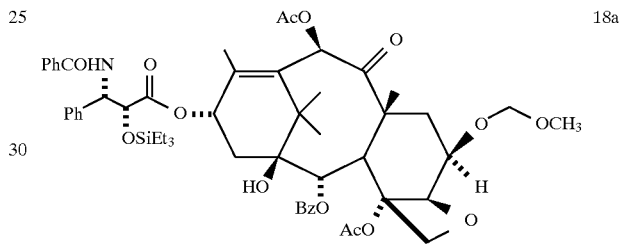

ESILRMS M+H calcd. for $C_{55}H_{70}O_{15}N$ Si: 1012. Found: 1012.

IR(KBr) 3445 (br.), 2955, 1731, 1670, 1483, 13 71, 1242 $cm^{-1}$.

Anal calcd. for $C_{55}H_{69}O_{15}$ N Si: C, 65.26; H, 6.87; N, 1.38. Found: C,65.23; H, 6.88; N, 1.33.

The silyl ether 18a (0.428 g, 0.423 mmol) was dissolved in 10 mL of $CH_3CN$ and cooled to 0° C. HCl (0.846 mL, 1N, 0.846 mmol) was added and the reaction was stirred at 0° C. for 1 hr. The reaction was quenched with $NaHCO_3$(sat), and extracted with ethyl acetate. The solution was dried over $MgSO_4$, filtered, and concentrated. The residue was chromatographed over silica gel (1:2 hexane/ethyl acetate) to give 0.343 g of methoxymethyl ether VIn (90%).

ESILRMS M+H calcd. for $C_{49}H_{56}O_{15}N$: 898. Found: 898.

IR(KBr) 3436(br.), 2930, 1730, 1664, 1485, 1371, 1241 $cm^{-1}$.

Anal calcd. for $C_{49}H_{55}O_{15}$ N: C, 65.54; H, 6.17; N, 1.56. Found: C, 65.52; H,6.22; N, 1.52.

EXAMPLE 1

Preparation of BMS-200659

To a suspension of intermediate II (hydrochloride salt) described above, 0.600 g, 0.67 mmol) in anhydrous THF (8 ml) cooled to 0° C. was added 2.0 ml of pyridine followed by orthonitrophenylsulfenylchloride (Aldrich, 0.14 g, 0.74 mmol) and finally DMAP (0.073 g, 0.58 mmol). The cooling bath was removed and the reaction mixture was stirred at room temperature for 2 h. A TLC taken at this time (1:1, hexanes:EtOAc) indicated the consumption of starting material and the formation of a higher running product. The reaction mixture was then diluted with ethyl acetate and washed sequentially with 0.1N HCl (aq), saturated sodium bicarbonate (aq) and brine. Each aqueous layer was then back extracted with ethyl acetate and the resulting organic layers were combined and dried over sodium sulfate. The dried organics were then concentrated in vacuo and the residual solid was purified via flash chromatograph (hexanes:ethyl acetate) to provide the desired product as yellow solid (480 mg, 71%). $^1$H NMR (CDCl$_3$, 300MHz)δ( 8.18–8.09 (3H, m), 8.04–7.90 (3H, m), 7.68–7.60 (2H, m), 7.54–7.36 (9H, m), 7.22–7.08 (2H, m), 6.22 (1H,s) 5.95 (1H, dd, J=9.1, 8.6 Hz) 5.57 (1H, d, J=7.1 Hz), 5.43 (1H, d, J=7.3 Hz), 4.92 (1H, d, J=8.5 Hz), 4.60 (1H, dd, J=6.9, 6.7 Hz), 4.39 (1H, m), 4.25 (1H, d, J=8.4 Hz), 4.09 (1H, d, J=8.5 Hz), 3.72 (1H, d, J=6.4 Hz), 3.64 (1H, d, J=6.9 Hz), 2.62–1.05 (22H, including singlets at 2.32, 2.18, 1.80, 1.62, 1.15, 1.05 ppm, 3H each).

EXAMPLE 2

Preparation of BMS-200273

A. Formation of 3-nitrophenylsulfenylchloride

Chlorine gas was bubbled through a solution of 3-nitrophenyldisulfide (1.0 g) in anhydrous dichloromethane (200 ml) at room temperature for a period of 60 minutes. The solution was then stirred for an additional 3 h at room temperature after which time the reaction mixture was purged with argon(g) to displace the chlorine gas. The resulting solution was then concentrated in vacuo and used as is in the next step.

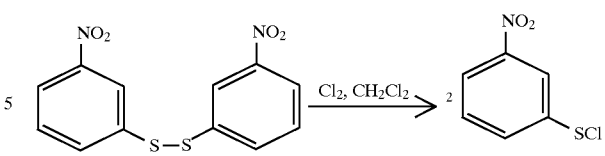

B. Preparation of BMS-200273

The crude 3-nitrophenylsulfenylchloride (0.506 g, 2.67 mmol) was added to a THF (10 ml) solution of intermediate II (1.0 g, 1.12 mmol) and 3 ml of pyridine cooled to 0° C. To the resulting solution was then added DMAP (0.111 g, 0.89 mmol) and the reaction mixture was warmed to room temperature and stirred for 3 h. The reaction mixture was then diluted with ethyl acetate and washed sequentially with aqueous solutions of 0.1N HCl, sodium bicarbonate and brine. The aqueous layers were then back extracted with ethyl acetate and the combined organics were dried over sodium sulfate and concentrated in vacuo. The resulting residual solid was purified via flash chromatography δ(hexanes:ethyl acetate) to provide the desired paclitaxel-C2'-benzoate-C3'-sulfenamide BMS-200273 as a yellow solid (510 mg, 45%). $^1$H NMR (CDCl$_3$)δ( 8.14–7.93 (5H, m), 7.85 (1H, m), 7.69–7.10 (13H, m) 6.20 (1H, s) 5.93 (1H, dd, J=8.9, 8.8 Hz), 5.57 (1H, d, J=7.1 Hz), 5.40 (1H, d, J=7.3 Hz), 4.92 (1H, d, J=8.8 Hz), 4.58 (1H, dd, J=7.2, 5.3 Hz), 4.40 (1H, m), 4.24 (1H, d, J=8.5 Hz), 4.10 (1H, d, J=8.4 Hz), 4.05 (1H, d, J=5.2 Hz), 3.65 (1H, d, J=7.0 Hz), 2.60–1.05 (22H, including singlets at 2.32, 2.18, 1.80, 1.61, 1.15, 1.05 ppm, 3H each).

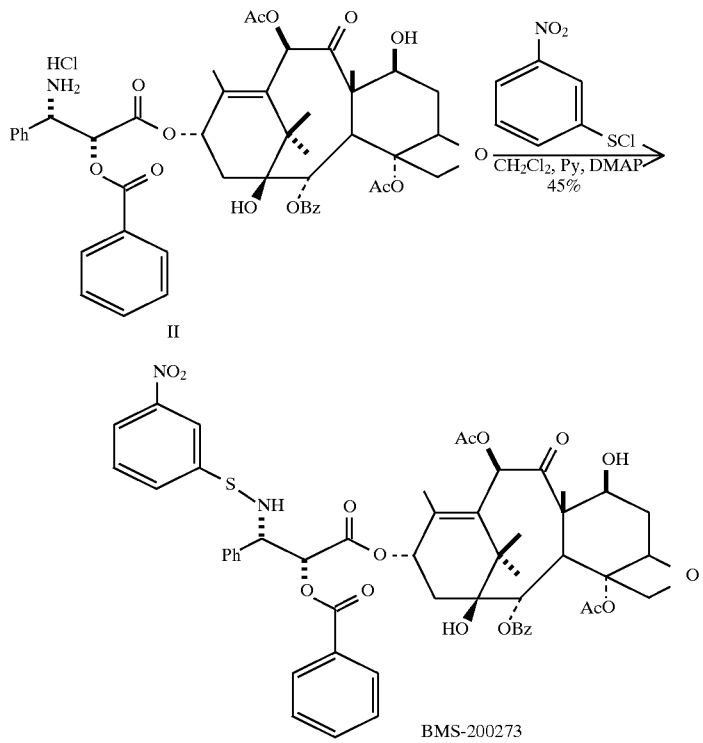

EXAMPLE 3

Preparation of BMS-200274

A. Formation of pyridine-2-sulfenylchloride

Chlorine gas was bubbled through a solution of pyridine-2-disulfide (Aldrich, 1.0 g, 4.54 mmol) in dichloromethane (200 ml) for a period of 60 minutes. At this time the reaction mixture was sealed using a rubber septa and stirred at room temperature for 18 h. The excess chlorine gas was then displaced from the reaction mixture with argon(g) over a 20 min period after which the solution was concentrated in vacuo to provide the desired pyridine-2-sulfenylchloride which was used as is in the next reaction.

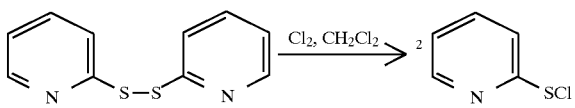

B. Preparation of BMS-200274

To a solution of intermediate II (hydrochloride salt) (1.0 g, 1.12 mmol) and 3 ml of pyridine in THF (10 ml) cooled to 0° C. was added pyridine-2 -sulfenylchloride (0.195 g, 1.34 mmol) followed by DMAP (0.111 g, 0.89 mmol) and the resulting solution was warmed to room temperature and stirred for 3 h. The reaction mixture was then diluted with ethyl acetate and washed sequentially with aqueous solutions of ammonium chloride, sodium bicarbonate and brine. The aqueous layers were each back extracted and the combined organics were dried over sodium sulfate, concentrated in vacuo and purified via flash chromatography (hexanes:ethyl acetate) to provide the desired sulfenamide, BMS-200274, as a white solid (453 mg, 42%). $^1$H NMR (CDCl$_3$) δ 8.50 (1H, m), 8.28 (2H, m), 8.05 (2H, m), 7.72–6.90 (14H, m), 6.21 (1H, s), 5.88 (1H, dd, J=8.7, 8.4 Hz), 5.59 (1H, d, J=7.1 Hz), 5.23 (1H, d, J=8.0 Hz), 4.92 (1H, d, J=8.1 Hz), 4.65 (1H, d, J=8.0 Hz), 4.58 (1H, br), 4.42 (1H, m), 4.20 (1H, d, J=8.4 Hz), 4.08 (1H, d, J=8.3 Hz), 3.65 (1H, d, J=7.0 Hz), 2.62–1.02 (22H, including singlets at 2.30, 2.15, 1.75, 1.60, 1.12, 1.05 ppm, 3H each).

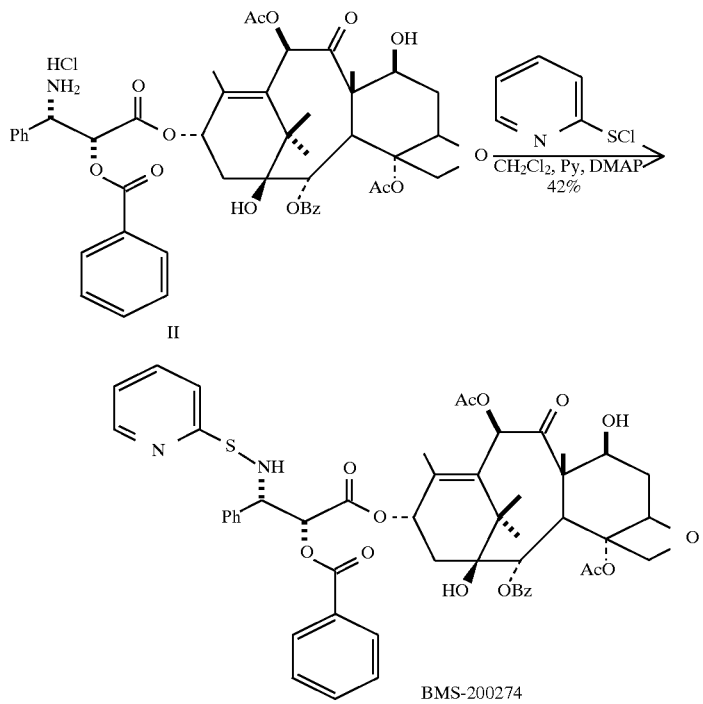

EXAMPLE 4

Preparation of BMS-200275

A. Formation of 5-Nitropyridine-2-sulfenylchloride.

Chlorine gas was bubbled through a solution of 2,2'-dithiobis(5-nitropyridine) (Aldrich, 1.1 g, 3.54 mmol) in dichloromethane (100 ml) for a period of 30 min. The resulting reaction mixture was then sealed using a rubber septa and stirred at room temperature for a period of 3 h. At this time excess chlorine was removed by purging the reaction mixture with argon(g) for a 20 min period and the resulting solution was concentrated in vacuo to provide the desired-5-nitro-pyridine-2-sulfenylchloride in crude form. This was used as is in the next step.

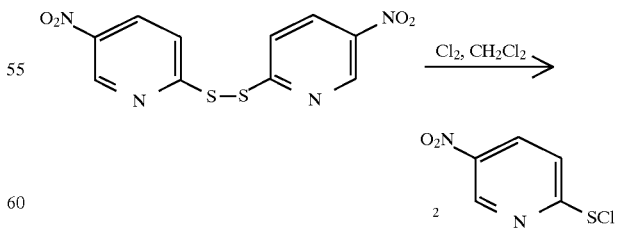

B. Preparation of BMS-200275

To a solution of intermediate II (hydrochloride salt) (1.0 g, 1.12 mmol), and 3 ml of pyridine in THF (10 ml) cooled to 0° C. was added 5-nitropyridine-2-sulfenylchloride (0.430 g, 2.23 mmol) followed by DMAP (0.115 g, 0.927 mmol). The resulting reaction mixture was warmed to room temperature and then diluted with 10 ml of THF and stirred for 3 h. The reaction mixture was then diluted with ethyl acetate and washed sequentially with aqueous solutions of saturated ammonium chloride, sodium bicarbonate and brine. The aqueous layers were then back extracted with ethyl acetate and the combined organics were dried over sodium sulfate, concentrated in vacuo and purified using flash chromatography to provide the desired sulfenamide (450 mg, 40%) as a light yellow solid. $^1$H NMR (CDCl$_3$), δ 9.25 (1H, m), 8.22–8.17 (3H, m), 8.14 (2H,m), 7.71–7.10 (12H, m), 6.20 (1H, s), 5.89 (1H, m), 5.57 (1H, d, J=7.2 Hz), 5.28 (1H, d, J=8.2 Hz), 4.94 (1H, d, 8.7 Hz), 4.70 (1H, m), 4.49 (1H, br), 4.92 (1H, m), 4.24 (1H, d, J=8.5 Hz), 4.10 (1H, d, J=8.4 Hz), 3.69 (1H, d, J=6.9 Hz), 2.60–1.02 (22H, including singlets at 3.31, 2.20, 1.82, 1.62, 1.15, 1.05 ppm, 3H each).

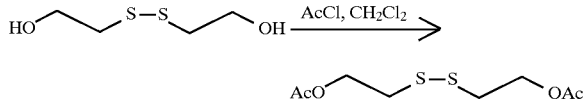

To a solution of the disulfide (1.0 g, 4.20 mmol) in anhydrous methylene chloride cooled to −30° C. was added a solution of chlorine in carbon tetrachloride (19.30 ml, 0.217M) and the resulting mixture was slowly warmed to 0° C. over 3 h. The reaction mixture was then concentrated in vacuo to provide the desired sulfenyl chloride. $^1$H NMR (CDCl$_3$, 300MHz) δ 4.40 (2H, m), 3.31 (2H, m), 2.05 (3H, m).

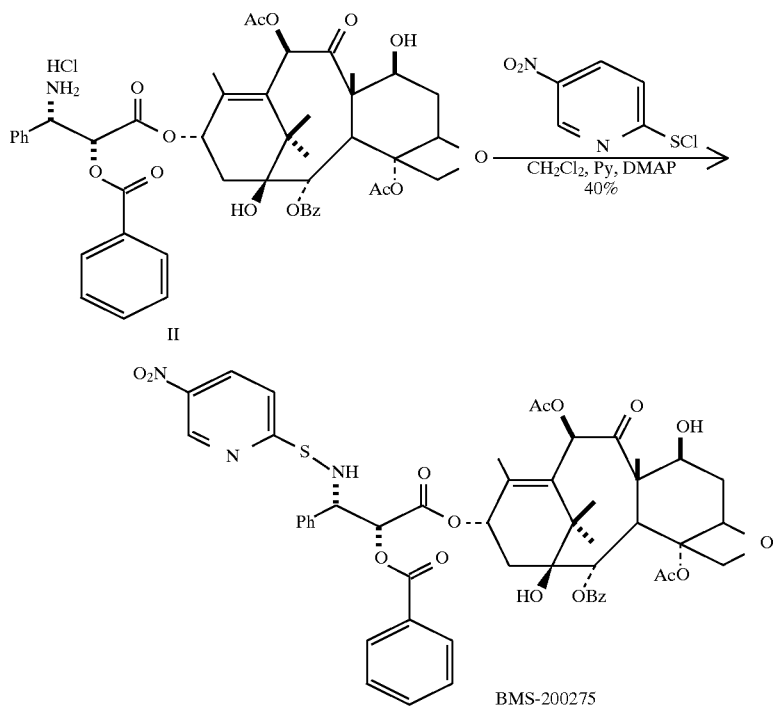

EXAMPLE 5

Preparation of BMS-204243 and BMS-204287

A. Preparation of Sulfenyl chloride

To a solution of bishydroxyethyldisulfide (5 g, 32.4 mmol) in dichloromethane (320 ml) cooled to 0° C. was added diethylisopropyl amine (28 ml, 160.8 mmol) followed by acetyl chloride (6.9 ml, 97.0 mmol) and the resulting solution was stirred for 14 h. The reaction mixture was then diluted with ethyl acetate and washed sequentially with saturated aqueous sodium bicarbonate, saturated ammonium chloride and brine. The organics were then dried over sodium sulfate and concentrated in vacuo. The crude bisacetate was purified using flash chromatography (hexane, ethyl acetate) to provide the desired disulfide compound (5.1 g, 66%). $^1$H NMR (CDCl$_3$, 300MHz) δ 4.29 (4H, m), 2.84 (4H, m), 2.03 (6H, s).

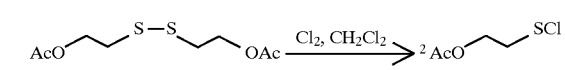

B. Preparation of BMS-204243 and BMS-204287

To a solution of intermediate 11 (1.0 g, 2.24 mmol) in anhydrous methylene chloride (20 ml) was added DMAP (274 mg, 2.24 mmol) and the resulting solution was cooled to −40° C. To this solution was then added the above sulfenyl chloride and the resulting solution was slowly warmed to room temperature over 2 h. The reaction mixture was then diluted with ethyl acetate and quenched by the addition of 0.1N HCl (aq). The organic layer was washed with saturated aqueous sodium bicarbonate followed by brine and subsequently dried over sodium sulfate. The organics were then concentrated in vacuo and the crude product mixture was purified via flash chromatography (hexanes, ethyl acetate) to provide the desired sulfenamide BMS-204243 (430 mg, 20%) and the bisadduct BMS-204287 (312 mg). $^1$H NMR BMS-204243 (CDCl$_3$, 300MHz) δ 8.12–8.01 (4H, m), 7.68–7.15 (12H, m), 6.22 (1H, s), 5.96 (1H, dd, J=9.1, 8.8 Hz), 5.59 (1H, d, J=7.0 Hz), 5.22 (1H, d, J=7.0Hz), 4.95 (1H, d, J=9.4 Hz), 4.55 (1H, dd, J=6.9, 6.9 Hz), 4.44–4.32 (1H, m), 4.30–4.15 (3H, m), 4.10 (1H, d, 8.5 Hz), 3.70 (1H, d, J=7.0 Hz), 3.62 (1H, d, J=5.3 Hz), 2.80–1.04 (27H, including singlets at 2.33, 2.20, 1.92, 1.85, 1.61, 1.18, 1.08, 3H each). $^1$H NMR BMS-204287 (CDCl$_3$, 300MHz) δ 8.20 (2H, m), 8.04 (2H, m), 7.70–7.14 (11H, m), 6.18 (1H, s), 5.81–5.70 (2H, m), 5.53 (1H, d, J=7.1 Hz), 4.93 (1H, d, J=8.0 Hz), 4.86 (1H, d, J=10.1 Hz), 4.44–4.36 (1H, m), 4.30 (1H, d, J=8.3 Hz), 4.22–4.08 (5H, m), 3.69 (1H, d, J=7.1 Hz) 2.95–2.80 (4H, m), 2.55–1.00 (28H, including singlets at 2.49 (3H), 2.15 (3H), 2.02 (6H), 1.69 (3H), 1.60 (3H), 1.10 (3H), 1.04 (3H).

mmol) and the resulting solution was cooled to 0° C. Methylchloromethylsulfenyl formate (Aldrich, 0.20 ml, 2.24 mmol) was then added and the resulting solution was stirred at 0° C. for 2 h. The reaction mixture was then diluted with ethyl acetate and washed with saturated ammonium chloride followed by brine. The organic extract was then dried over sodium sulfate and concentrated in vacuo. The residual oil was purified via flash chromatography (hexanes:ethyl acetate) to provide the desired aminyl thiocarbonate (1.1 g, 52%). $^1$H NMR (CDCl$_3$, 300MHz) δ 8.17 (2H, m), 8.06 (2H, m), 7.71–7.31 (10H, m), 7.16 (1H, m), 6.24 (1H, s), 5.95 (1H, dd, J=9.1, 8.4 Hz), 5.58 (1H, d, J=7.1 Hz), 5.18 (1H, d, J=7.7 Hz), 4.94 (1H, d, J=7.9 Hz), 4.70 (1H, d, J=7.6 Hz),

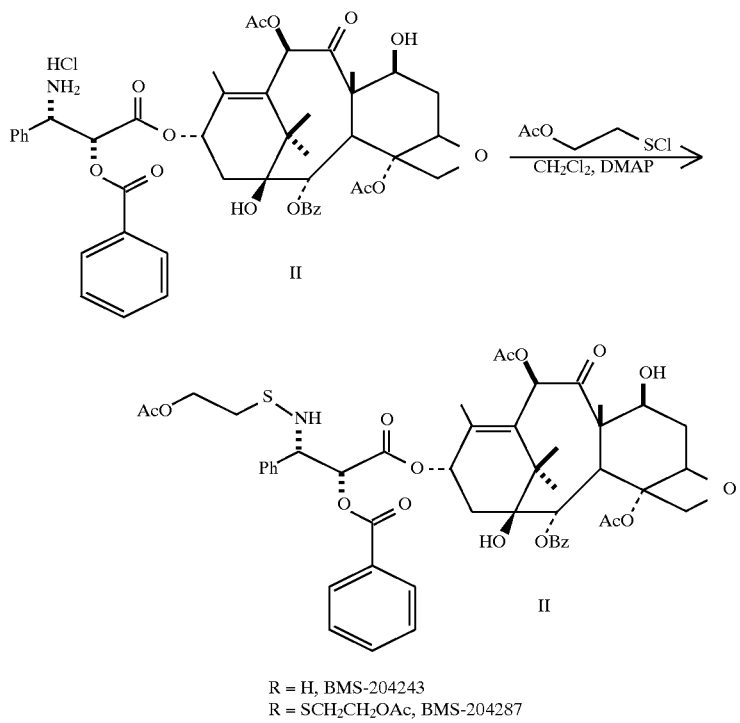

R = H, BMS-204243
R = SCH$_2$CH$_2$OAc, BMS-204287

EXAMPLE 6

Preparation of BMS-204126

To a solution of intermediate II (2.0 g, 2.24 mmol) in methylene chloride (20 ml) was added DMAP (411 mg, 3.36

4.43 (1H, m), 4.25 (1H, d, J=8.4 Hz), 4.12 (1H, d, J=8.4 Hz), 4.05 (1H, s), 3.75 (3H, s), 3.70 (1H, d, J=7.0 Hz), 2.61–1.04 (22H, including singlets at 2.35, 2.20, 1.82, 1.63, 1.19, 1.04, 3H each).

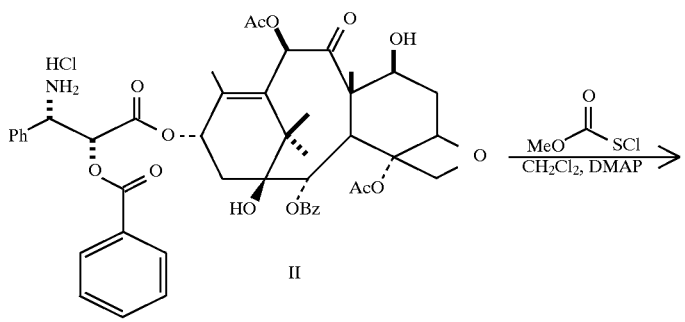

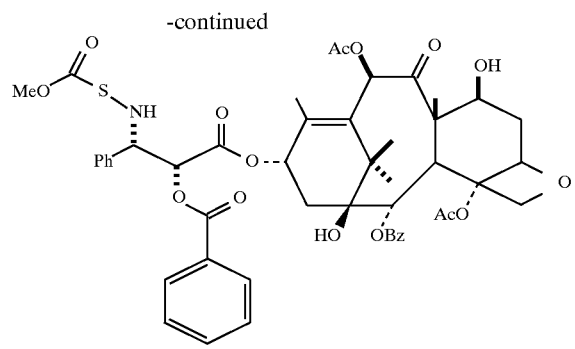

BMS-204128

Following the general procedures illustrated in Examples 1–16 above, the following additional examples may be prepared:

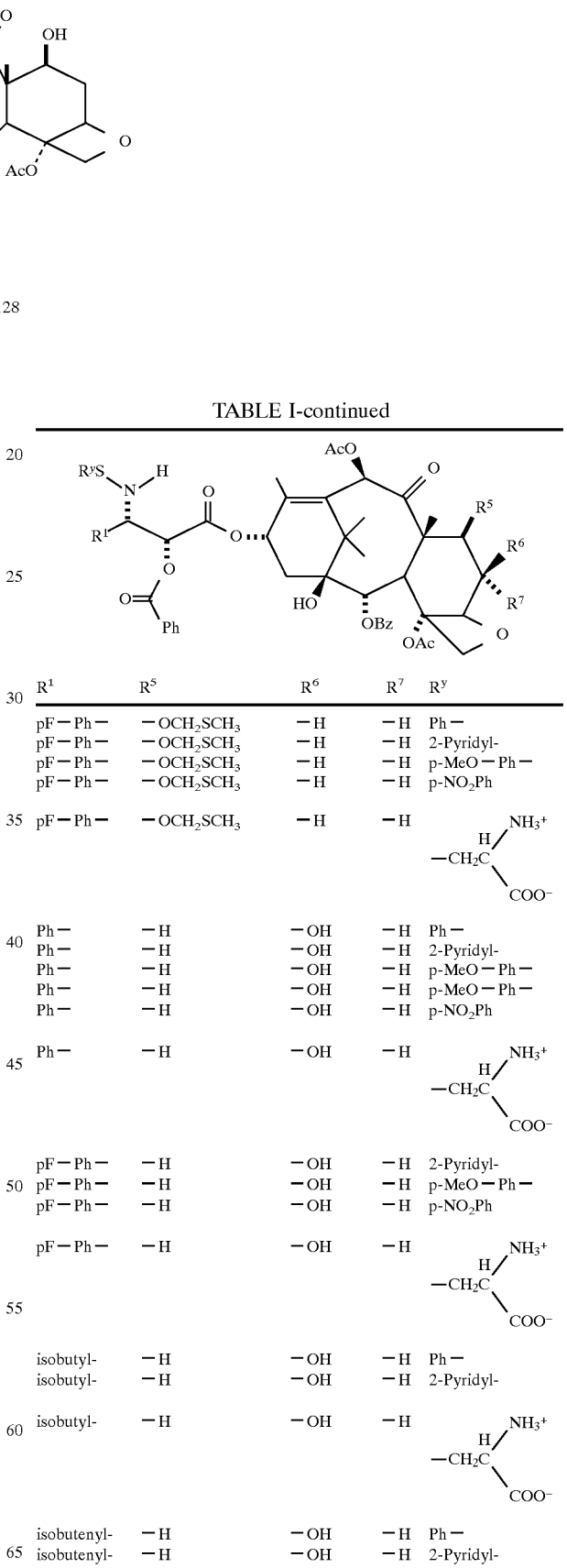

TABLE I

| $R^1$ | $R^5$ | $R^6$ | $R^7$ | $R^y$ |
|---|---|---|---|---|
| Ph— | —OCH$_2$OCH$_3$ | —H | —H | Ph— |
| Ph— | —OCH$_2$OCH$_3$ | —H | —H | 2-Pyridyl- |
| Ph— | —OCH$_2$OCH$_3$ | —H | —H | p-MeO—Ph— |
| Ph— | —OCH$_2$OCH$_3$ | —H | —H | p-NO$_2$Ph |
| Ph— | —OCH$_2$OCH$_3$ | —H | —H | —CH$_2$C(H)(NH$_3^+$)(COO$^-$) |
| pF—Ph— | —OCH$_2$OCH$_3$ | —H | —H | Ph— |
| pF—Ph— | —OCH$_2$OCH$_3$ | —H | —H | 2-Pyridyl- |
| pF—Ph— | —OCH$_2$OCH$_3$ | —H | —H | p-MeO—Ph— |
| pF—Ph— | —OCH$_2$OCH$_3$ | —H | —H | p-NO$_2$Ph |
| pF—Ph— | —OCH$_2$OCH$_3$ | —H | —H | —CH$_2$C(H)(NH$_3^+$)(COO$^-$) |
| Ph— | —OH | —H | —H | p-MeO—Ph— |
| Ph— | —OH | —H | —H | p-NO$_2$Ph |
| Ph— | —OCH$_2$SCH$_3$ | —H | —H | Ph— |
| Ph— | —OCH$_2$SCH$_3$ | —H | —H | 2-Pyridyl- |
| Ph— | —OCH$_2$SCH$_3$ | —H | —H | —CH$_2$C(H)(NH$_3^+$)(COO$^-$) |
| Ph— | —OCH$_2$SCH$_3$ | —H | —H | p-MeO—Ph— |
| Ph— | —OCH$_2$SCH$_3$ | —H | —H | p-NO$_2$Ph |
| Ph— | —OCH$_2$SCH$_3$ | —H | —H | —CH$_2$C(H)(NH$_3^+$)(COO$^-$) |
| pF—Ph— | —OCH$_2$SCH$_3$ | —H | —H | Ph— |
| pF—Ph— | —OCH$_2$SCH$_3$ | —H | —H | 2-Pyridyl- |
| pF—Ph— | —OCH$_2$SCH$_3$ | —H | —H | p-MeO—Ph— |
| pF—Ph— | —OCH$_2$SCH$_3$ | —H | —H | p-NO$_2$Ph |
| pF—Ph— | —OCH$_2$SCH$_3$ | —H | —H | —CH$_2$C(H)(NH$_3^+$)(COO$^-$) |
| Ph— | —H | —OH | —H | Ph— |
| Ph— | —H | —OH | —H | 2-Pyridyl- |
| Ph— | —H | —OH | —H | p-MeO—Ph— |
| Ph— | —H | —OH | —H | p-MeO—Ph— |
| Ph— | —H | —OH | —H | p-NO$_2$Ph |
| Ph— | —H | —OH | —H | —CH$_2$C(H)(NH$_3^+$)(COO$^-$) |
| pF—Ph— | —H | —OH | —H | 2-Pyridyl- |
| pF—Ph— | —H | —OH | —H | p-MeO—Ph— |
| pF—Ph— | —H | —OH | —H | p-NO$_2$Ph |
| pF—Ph— | —H | —OH | —H | —CH$_2$C(H)(NH$_3^+$)(COO$^-$) |
| isobutyl- | —H | —OH | —H | Ph— |
| isobutyl- | —H | —OH | —H | 2-Pyridyl- |
| isobutyl- | —H | —OH | —H | —CH$_2$C(H)(NH$_3^+$)(COO$^-$) |
| isobutenyl- | —H | —OH | —H | Ph— |
| isobutenyl- | —H | —OH | —H | 2-Pyridyl- |

TABLE I-continued

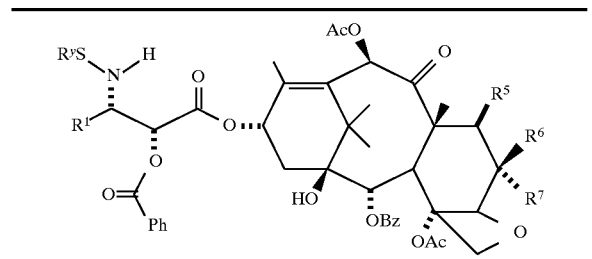

| R¹ | R⁵ | R⁶ | R⁷ | Rʸ |
|---|---|---|---|---|
| isobutenyl- | —H | —OH | —H | —CH₂C(H)(NH₃⁺)COO⁻ |
| 2-furyl- | —H | —OH | —H | Ph— |
| 2-furyl- | —H | —OH | —H | 2-Pyridyl- |
| 2-furyl- | —H | —OH | —H | —CH₂C(H)(NH₃⁺)COO⁻ |
| isopropyl | —H | —OH | —H | Ph— |
| isopropyl | —H | —OH | —H | 2-Pyridyl- |
| isopropyl | —H | —OH | —H | —CH₂C(H)(NH₃⁺)COO⁻ |
| cyclopropyl | —H | —OH | —H | Ph— |
| cyclopropyl | —H | —OH | —H | 2-Pyridyl- |
| cyclopropyl | —H | —OH | —H | —CH₂C(H)(NH₃⁺)COO⁻ |
| Ph— | —H | —H | —OH | Ph— |
| Ph— | —H | —H | —OH | 2-Pyridyl- |
| Ph— | —H | —H | —OH | p-MeO—Ph— |
| Ph— | —H | —H | —OH | p-NO₂Ph |
| Ph— | —H | —H | —OH | —CH₂C(H)(NH₃⁺)COO⁻ |
| pF—Ph— | —H | —H | —OH | Ph— |
| pF—Ph— | —H | —H | —OH | 2-Pyridyl- |
| pF—Ph— | —H | —H | —OH | p-MeO—Ph— |
| pF—Ph— | —H | —H | —OH | p-NO₂Ph |
| pF—Ph— | —H | —H | —OH | —CH₂C(H)(NH₃⁺)COO⁻ |
| isobutyl- | —H | —H | —OH | Ph— |
| isobutyl- | —H | —H | —OH | 2-Pyridyl- |
| isobutyl- | —H | —H | —OH | —CH₂C(H)(NH₃⁺)COO⁻ |
| isobutenyl- | —H | —H | —OH | Ph— |
| isobutenyl- | —H | —H | —OH | 2-Pyridyl- |

TABLE I-continued

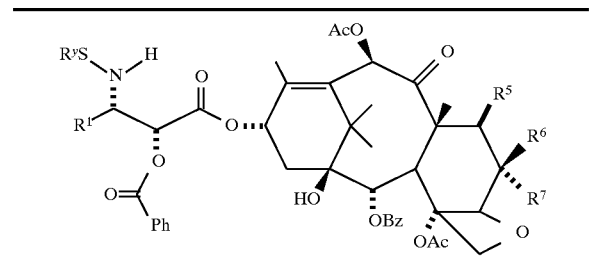

| R¹ | R⁵ | R⁶ | R⁷ | Rʸ |
|---|---|---|---|---|
| isobutenyl- | —H | —H | —OH | —CH₂C(H)(NH₃⁺)COO⁻ |
| 2-furyl- | —H | —H | —OH | Ph— |
| 2-furyl- | —H | —H | —OH | 2-Pyridyl- |
| 2-furyl- | —H | —H | —OH | —CH₂C(H)(NH₃⁺)COO⁻ |
| isopropyl | —H | —H | —OH | Ph— |
| isopropyl | —H | —H | —OH | 2-Pyridyl- |
| isopropyl | —H | —H | —OH | —CH₂C(H)(NH₃⁺)COO⁻ |
| cyclopropyl | —H | —H | —OH | Ph— |
| cyclopropyl | —H | —H | —OH | 2-Pyridyl- |
| cyclopropyl | —H | —H | —OH | —CH₂C(H)(NH₃⁺)COO⁻ |
| Ph— | —H | —OCH₂OCH₃ | —H | Ph— |
| Ph— | —H | —OCH₂OCH₃ | —H | 2-Pyridyl- |
| Ph— | —H | —OCH₂OCH₃ | —H | p-MeO—Ph— |
| Ph— | —H | —OCH₂OCH₃ | —H | p-NO₂Ph |
| Ph— | —H | —OCH₂OCH₃ | —H | —CH₂C(H)(NH₃⁺)COO⁻ |
| pF—Ph— | —H | —OCH₂OCH₃ | —H | Ph— |
| pF—Ph— | —H | —OCH₂OCH₃ | —H | 2-Pyridyl- |
| pF—Ph— | —H | —OCH₂OCH₃ | —H | p-MeO—Ph— |
| pF—Ph— | —H | —OCH₂OCH₃ | —H | p-NO₂Ph |
| pF—Ph— | —H | —OCH₂OCH₃ | —H | —CH₂C(H)(NH₃⁺)COO⁻ |
| isobutyl- | —H | —OCH₂OCH₃ | —H | Ph— |
| isobutyl- | —H | —OCH₂OCH₃ | —H | 2-Pyridyl- |
| isobutyl- | —H | —OCH₂OCH₃ | —H | —CH₂C(H)(NH₃⁺)COO⁻ |
| isobutenyl- | —H | —OCH₂OCH₃ | —H | Ph— |
| isobutenyl- | —H | —OCH₂OCH₃ | —H | 2-Pyridyl- |

TABLE I-continued

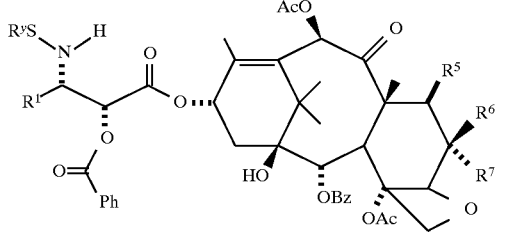

| R¹ | R⁵ | R⁶ | R⁷ | Rʸ |
|---|---|---|---|---|
| isobutenyl- | —H | —OCH₂OCH₃ | —H | —CH₂C(H)(NH₃⁺)COO⁻ |
| 2-furyl- | —H | —OCH₂OCH₃ | —H | Ph— |
| 2-furyl- | —H | —OCH₂OCH₃ | —H | 2-Pyridyl- |
| 2-furyl- | —H | —OCH₂OCH₃ | —H | —CH₂C(H)(NH₃⁺)COO⁻ |
| isopropyl- | —H | —OCH₂OCH₃ | —H | Ph— |
| isopropyl- | —H | —OCH₂OCH₃ | —H | 2-Pyridyl- |
| isopropyl- | —H | —OCH₂OCH₃ | —H | —CH₂C(H)(NH₃⁺)COO⁻ |
| cyclopropyl | —H | —OCH₂OCH₃ | —H | Ph— |
| cyclopropyl | —H | —OCH₂OCH₃ | —H | 2-Pyridyl- |
| cyclopropyl | —H | —OCH₂OCH₃ | —H | —CH₂C(H)(NH₃⁺)COO⁻ |
| Ph— | —H | —OH | —CH₃ | Ph— |
| Ph— | —H | —OH | —CH₃ | 2-Pyridyl |
| Ph— | —H | -ketone | | Ph— |
| Ph— | —H | -ketone | | 2-Pyridyl |
| Ph— | —H | —OC(O)₂Et | —H | Ph— |
| Ph— | —H | —OC(O)₂Me | —H | Ph— |
| Ph— | —H | —OC(O)₂Me | —H | —CH₂C(H)(NH₃⁺)COO⁻ |

TABLE II

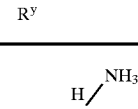

| R¹ | Rᵈ | L | R⁹ | Rʸ |
|---|---|---|---|---|
| Ph | —OMe | O | Ph | Ph— |
| Ph | —OMe | O | Ph | 2-Pyridyl- |
| Ph | —OMe | O | Ph | p-MeO—Ph— |
| Ph | —OMe | O | Ph | p-NO₂Ph |
| Ph | —OMe | O | Ph | —CH₂C(H)(NH₃⁺)COO⁻ |
| Ph | —OEt | O | Ph | Ph— |
| Ph | —OEt | O | Ph | 2-Pyridyl- |
| Ph | —OEt | O | Ph | p-MeO—Ph— |
| Ph | —OEt | O | Ph | p-NO₂Ph |
| Ph | —OEt | O | Ph | Ph— |
| Ph | —OEt | O | Ph | 2-Pyridyl- |
| Ph | —OEt | O | Ph | p-MeO—Ph— |
| Ph | —OEt | O | Ph | p-NO₂Ph |
| Ph | —OEt | O | Ph | —CH₂C(H)(NH₃⁺)COO⁻ |
| Ph | —OnPr | O | Ph | Ph— |
| Ph | —OnPr | O | Ph | 2-Pyridyl- |
| Ph | —OnPr | O | Ph | p-MeO—Ph— |
| Ph | —OnPr | O | Ph | p-NO₂Ph |
| Ph | —OnPr | O | Ph | —CH₂C(H)(NH₃⁺)COO⁻ |
| Ph | —nPr | O | Ph | Ph— |
| Ph | —nPr | O | Ph | 2-Pyridyl- |
| Ph | —nPr | O | Ph | p-MeO—Ph— |
| Ph | —nPr | O | Ph | p-NO₂Ph |
| Ph | —nPr | O | Ph | —CH₂C(H)(NH₃⁺)COO⁻ |
| Ph | —cPr | O | Ph | Ph— |
| Ph | —cPr | O | Ph | 2-Pyridyl- |
| Ph | —cPr | O | Ph | —CH₂C(H)(NH₃⁺)COO⁻ |
| Ph | —Et | O | Ph | Ph— |
| Ph | —Et | O | Ph | 2-Pyridyl- |

TABLE II-continued

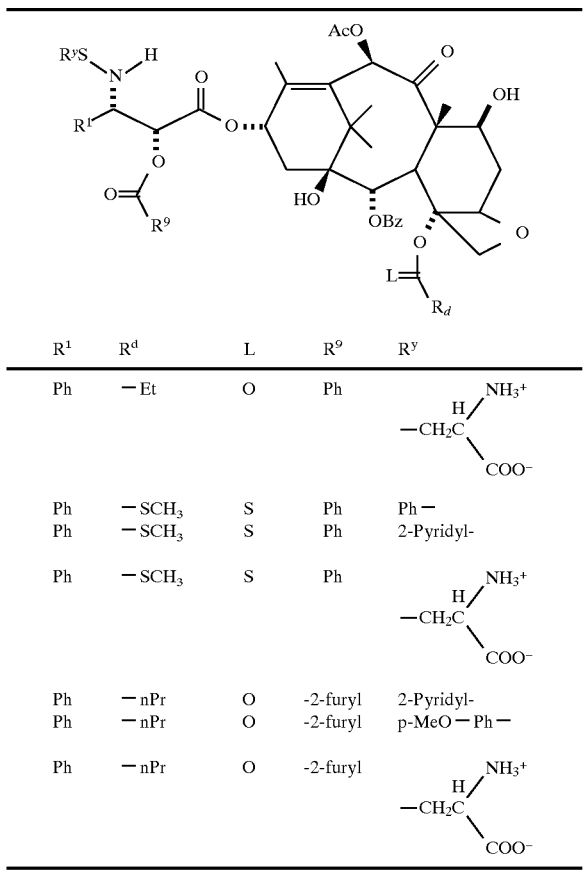

| R¹ | R_d | L | R⁹ | R^y |
|---|---|---|---|---|
| Ph | —Et | O | Ph | —CH₂C(H)(NH₃⁺)COO⁻ |
| Ph | —SCH₃ | S | Ph | Ph— |
| Ph | —SCH₃ | S | Ph | 2-Pyridyl- |
| Ph | —SCH₃ | S | Ph | —CH₂C(H)(NH₃⁺)COO⁻ |
| Ph | —nPr | O | -2-furyl | 2-Pyridyl- |
| Ph | —nPr | O | -2-furyl | p-MeO—Ph— |
| Ph | —nPr | O | -2-furyl | —CH₂C(H)(NH₃⁺)COO⁻ |

TABLE III

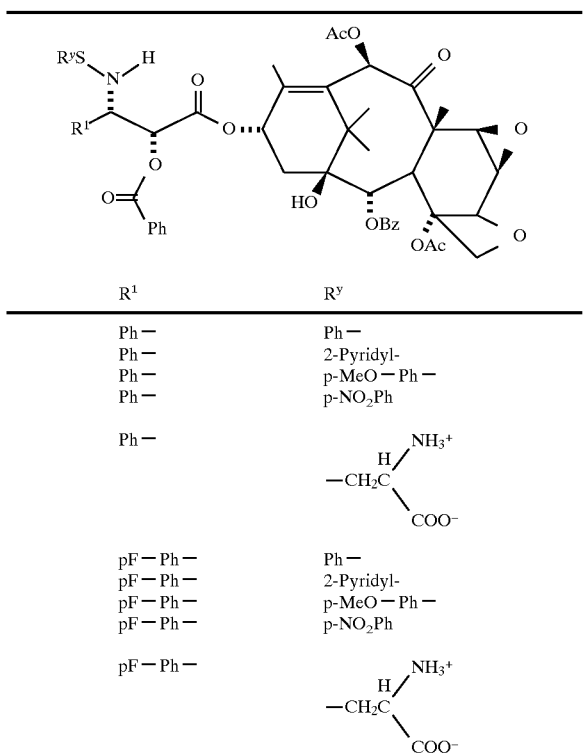

| R¹ | R^y |
|---|---|
| Ph— | Ph— |
| Ph— | 2-Pyridyl- |
| Ph— | p-MeO—Ph— |
| Ph— | p-NO₂Ph |
| Ph— | —CH₂C(H)(NH₃⁺)COO⁻ |
| pF—Ph— | Ph— |
| pF—Ph— | 2-Pyridyl- |
| pF—Ph— | p-MeO—Ph— |
| pF—Ph— | p-NO₂Ph |
| pF—Ph— | —CH₂C(H)(NH₃⁺)COO⁻ |

TABLE III-continued

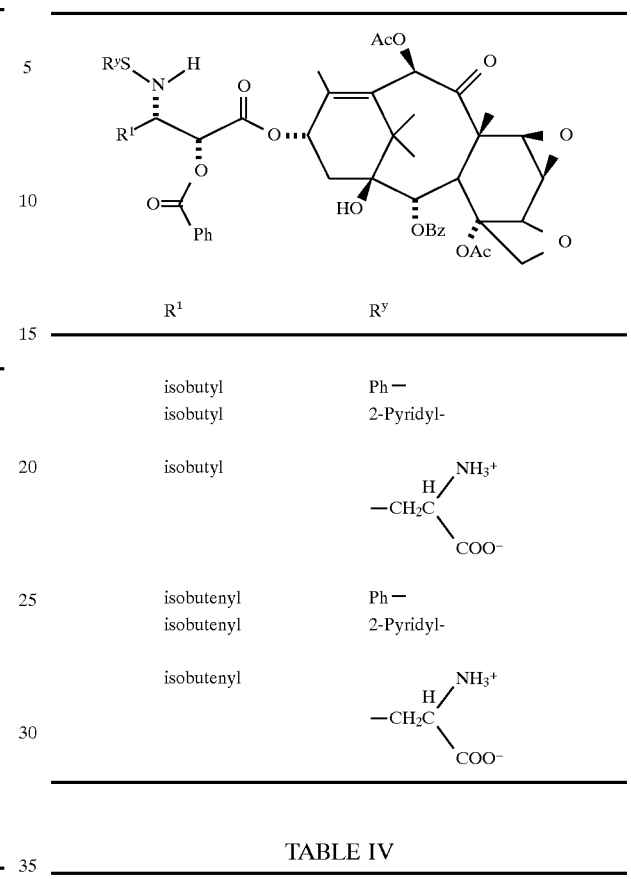

| R¹ | R^y |
|---|---|
| isobutyl | Ph— |
| isobutyl | 2-Pyridyl- |
| isobutyl | —CH₂C(H)(NH₃⁺)COO⁻ |
| isobutenyl | Ph— |
| isobutenyl | 2-Pyridyl- |
| isobutenyl | —CH₂C(H)(NH₃⁺)COO⁻ |

TABLE IV

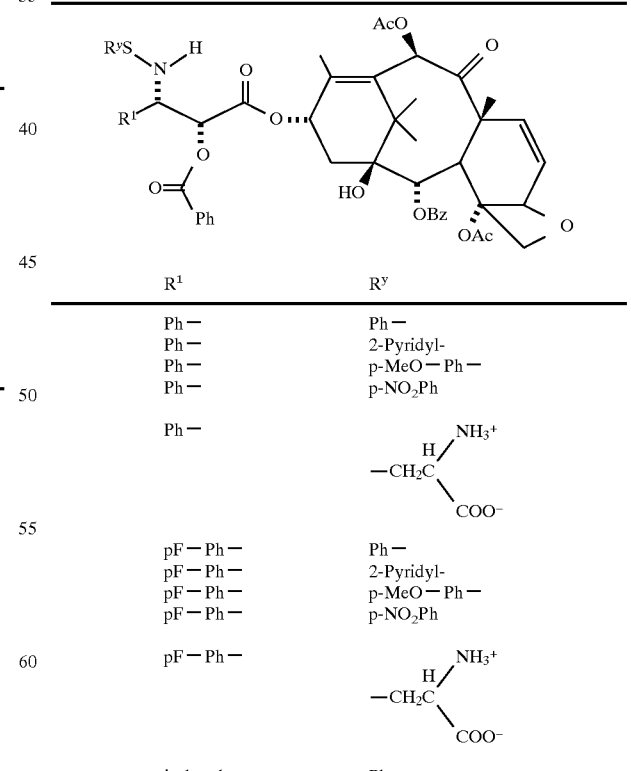

| R¹ | R^y |
|---|---|
| Ph— | Ph— |
| Ph— | 2-Pyridyl- |
| Ph— | p-MeO—Ph— |
| Ph— | p-NO₂Ph |
| Ph— | —CH₂C(H)(NH₃⁺)COO⁻ |
| pF—Ph— | Ph— |
| pF—Ph— | 2-Pyridyl- |
| pF—Ph— | p-MeO—Ph— |
| pF—Ph— | p-NO₂Ph |
| pF—Ph— | —CH₂C(H)(NH₃⁺)COO⁻ |
| isobutyl | Ph— |
| isobutyl | 2-Pyridyl- |

TABLE IV-continued

[Structure: taxane derivative with R¹ and RʸS-NH- substituents, AcO, OBz, OAc, HO, O=C-Ph groups]

| R¹ | Rʸ |
|---|---|
| isobutyl | —CH₂C(H)(NH₃⁺)COO⁻ |
| isobutenyl | Ph— |
| isobutenyl | 2-Pyridyl- |
| isobutenyl | —CH₂C(H)(NH₃⁺)COO⁻ |

TABLE V

[Structure: taxane derivative with R¹, R⁹, and RʸS-NH- substituents, AcO, OBz, OAc, HO groups]

| R¹ | R⁹ | Rʸ |
|---|---|---|
| Ph— | Ph— | Ph— |
| Ph— | Ph— | 2-Pyridyl- |
| Ph— | Ph— | p-MeO—Ph— |
| Ph— | Ph— | p-NO₂Ph |
| Ph— | Ph— | —CH₂C(H)(NH₃⁺)COO⁻ |
| pF—Ph— | Ph— | Ph— |
| pF—Ph— | Ph— | 2-Pyridyl- |
| pF—Ph— | Ph— | p-MeO—Ph— |
| pF—Ph— | Ph— | p-NO₂Ph |
| pF—Ph— | Ph— | —CH₂C(H)(NH₃⁺)COO⁻ |
| isobutyl | Ph— | Ph— |
| isobutyl | Ph— | 2-Pyridyl- |
| isobutyl | Ph— | —CH₂C(H)(NH₃⁺)COO⁻ |

TABLE V-continued

[Structure: taxane derivative with R¹, R⁹, and RʸS-NH- substituents, AcO, OBz, OAc, HO groups]

| R¹ | R⁹ | Rʸ |
|---|---|---|
| isobutenyl | Ph— | Ph— |
| isobutenyl | Ph— | 2-Pyridyl- |
| Ph— | isopentyl- | Ph— |

Representative in vivo Antitumor Activity

The compounds of the present invention are effective tumor-inhibiting agents and are useful in human and/or veterinary medicine. For example, they are effective in treating tumors in an in vivo assay described in EP 604,910 A1 published Jul. 6, 1994. In one test, Balb/c×DBA₂ $F_1$(CDF$_1$) hybrid mice were implanted subcutaneously (sc) with 0.1 ml of a 2% (w/v) brei of M109 lung carcinoma (as described by W. Rose in *Cancer Treatment Reports*, 65, No. 3–4, pp. 299–312 (1981). The test compounds and reference drug (paclitaxel) are administered intravenously to groups of mice; each group receives a compound at a different dose level, and three or four different dose levels are evaluated per compound.

Mice are followed daily for survival until their death or about day 90 post tumor implant, whichever comes first. One group of mice per experiment remain untreated and serve as the control. Tumors are also measured once or twice weekly and the size in mm is used to estimate tumor weight according to the published procedure. Median survival times of compound-treated (T) mice are compared to the median survival time of parallel control (C) mice. The ratio of the two values for each compound-treated group of mice is multiplied by 100 and expressed as a percentage, i.e. % T/C. Additionally, the difference between the median time for treated groups and that for the control group to grow tumor to 1 gm, expressed as T–C values in days, is also determined. The greater the T–C value, the greater the delay in primary tumor growth. Compounds showing % T/C ( 125% and/or T–C (4.0 days are considered to be active in this M109 sc model.

As shown below the representative compound of Example 1 was active against sc M109.

| Compound of Ex. 1 vs. Paclitaxel in SC M109 model | | | | | |
|---|---|---|---|---|---|
| Compound of Ex. 1 | | | Paclitaxel | | |
| Dose (mg/kg/inj)[1] | T-C (days) | % T/C | Dose (mg/kg/inj) | T-C (days) | % T/C |
| 64 | 21.3 | 164 | 24 | 17.5 | 227 |
| 32 | 16.0 | 156 | 18 | 19.5 | 137 |

[1]All dosing was qd 4–8

In another test mice were treated with representative compounds under study by receiving intraperitoneal injections of various doses on days 5 and 8 post-implant. Mice were followed daily for survival until approximately 75–90 days post-tumor implant. One group of mice per experiment remained untreated and served as the control group.

Data for two representative compounds and paclitaxel as the reference compound are shown below in this ip/ip M109 lung carcinoma model:

| | ip/ip M109 | | | ip/ip M109 | |
|---|---|---|---|---|---|
| Compound | Dose[1] | % T/C | Compound | Dose[1] | % T/C |
| paclitaxel | 60 | 145 | paclitaxel | 60 | 191 |
| | 40 | 138 | | 40 | 120 |
| Example 1 | 200 | 176 | Example 3 | 200 | 209 |
| | 100 | 148 | | 100 | 194 |

[1]mg/kg/inj on days 5 and 8

Another aspect of the present invention concerns a method for inhibiting human and/or other mammalian tumors which comprises administering to a tumor host an antitumor effective amount of a compound of the present invention.

For treating a variety of tumors, a compound of the present invention may be used in a manner similar to that of paclitaxel, e.g. see *Physician's Desk Reference*, 49th Edition, Medical Economics, p. 682, 1995. The dosage, mode and schedule of administration for the compound are not particularly restricted; an oncologist skilled in the art of cancer treatment will be able to ascertain, without undue experimentation, an appropriate treatment protocol. Thus, the compound may be administered via any suitable route of administration, parenteral or oral. Parenteral administration includes intravenous, intraperitoneal, intramuscular and subcutaneous administration.

The dosage may be, for example, in the range of about 10 to about 100 mg/kg of body weight or about 20 to about 500 mg/m$^2$. The actual dose used will vary according to the particular composition formulated, the route of administration and the particular site, host and type of tumor being treated. Many factors that modify the action of the drug will be taken into account in determining the dosage including age, weight, sex, diet and the physical condition of the patient.

The present invention also provides pharmaceutical compositions (formulations) containing an antitumor effective amount of a compound of the present invention with one or more pharmaceutically acceptable carriers, excipients, diluents or adjuvants. Examples of formulating paclitaxel or derivatives thereof may be found in, for example, U.S. Pat. Nos. 4,960,790 and 4,814,470, and such examples may be followed to formulate the compounds of this invention. For example, compounds of the present invention may be formulated in the form of tablets, pills, powder mixtures, capsules, injectables, solutions, suppositories, emulsions, dispersions, food premix, and in other suitable forms. They may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, mannitol, urea, dextrans, lactose, potato and maize starches, magnesium stearate, talc, vegetable oils, polyalkylene glycols, ethyl cellulose, polyvinylpyrrolidone, calcium carbonate, ethyl oleate, isopropyl myristate, benzyl benzoate, sodium carbonate, gelatin, potassium carbonate and silicic acid. The pharmaceutical preparation may also contain nontoxic auxiliary substances such as emulsifying, preserving or wetting agents and the like, for example, sorbitan monolaurate, triethanolamine oleate, polyoxyethylene monostearate, glyceryl tripalmitate, and dioctyl sodium sulfosuccinate.

We claim:
1. A compound of the formula

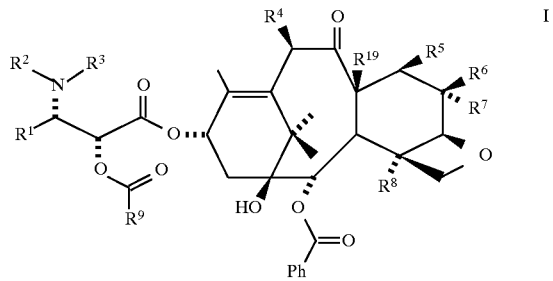

wherein
$R^1$ is $C_{1-6}$ alkyl, $C_{2-6}$ alkenyl, $C_{3-6}$ cycloalkyl or a radical of the formula —W—$R^x$ in which W is a bond, $C_{2-6}$ alkenediyl or —(CH$_2$)$_t$— in which t is an integer of from one to six and $R^x$ is naphthyl, phenyl or heteroaryl, said $R^x$ group being optionally substituted by 1 to 3 same or different $C_{1-6}$ alkyl, $C_{1-6}$ alkoxy, halogen or —CF$_3$ groups;

$R^2$ and $R^3$ are each independently hydrogen or a sulfenamide of the formula —$SR^y$ in which $R^y$ is aryl, substituted aryl, heteroaryl, substituted heteroaryl, $C_{1-6}$ alkyl having a terminal $C_{1-6}$ alkoxy or $C_{1-6}$ alkanoyloxy group and being optionally substituted by an oxo group, or $C_{1-6}$ alkyl substituted by both a carboxyl and amino group, providing that $R^2$ and $R^3$ may not both be hydrogen;

$R^4$ is hydrogen, hydroxy or —C(O)CH$_3$;

$R^5$ is hydrogen, hydroxy, —O—$C_{1-6}$ alkyl,
—C(O)$R_a$, —OC(O)O$R_a$, —OC(O)NH$R_a$,
—OC(O)N$R_b R_c$, —OCH$_2$O$R^1$ wherein $R^1$ is as defined above,
—OCHR$_a$O$R^1$ where $R^1$ is as defined above,
—OCH$_2$SCH$_3$, —OCH$_2$OCH$_2$SCH$_3$, —OP(O)(OH)$_2$,
—OCH$_2$OP(O)(OH)$_2$, —OCH$_2$OCH$_2$OP(O)(OH)$_2$,
—OC($R_a$)$_2$ S$R^1$ where $R^1$ is as defined above, or
—OCHR$_a$S$R^1$ where $R^1$ is as defined above;

$R_a$ is $C_{1-6}$ alkyl, $C_{2-6}$ alkenyl, $C_{2-6}$ alkynyl or $C_{3-6}$ cycloalkyl, any of which groups can be optionally substituted with one to six of the same or different halogen atoms;

$R_b$ and $R_c$ are each independently hydrogen, —CH$_3$, —CH$_2$CH$_2$— or benzyl, or $R_b$ and $R_c$ together with the nitrogen of N$R_b R_c$ form a pyrrolidino, piperidino, morpholino or N-methylpiperazino group;

$R^6$ and $R^7$ are each independently hydrogen, hydroxy, —$C_{1-6}$ alkyl or $R^5$, or $R^5$ and $R^6$ form an epoxide and $R^7$ is hydrogen, or $R^5$ and $R^6$ form a bond and $R^7$ is hydrogen;

$R^{19}$ is methyl or hydroxymethyl, or $R^{19}$ and $R^5$ together can form a cyclopropane ring in which case $R^6$ and $R^7$ are both hydrogen;

$R^8$ is

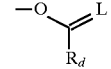

where L is O or S and $R_d$ is $C_{1-6}$ alkyl, $C_{2-6}$ alkenyl, $C_{2-6}$ alkynyl, $C_{3-6}$ cycloalkyl, $C_{3-6}$ cycloalkenyl, heteroaryl, —O—$C_{1-6}$ alkyl, —O—$C_{2-6}$ alkenyl, —O—$C_{2-6}$ alkynyl, —CH$_2$OCH$_3$, —CH$_2$OCH$_2$OCH$_3$, —CH$_2$OCH$_2$OCH$_2$CH$_3$, —CH$_2$CH$_2$OCH$_3$, or —S—$C_{1-6}$ alkyl; and $R^9$ is aryl, substituted aryl, cycloalkyl, $C_{1-6}$ alkyl, heteroaryl or substituted heteroaryl; or a pharmaceutically acceptable salt thereof.

2. A compound of the formula

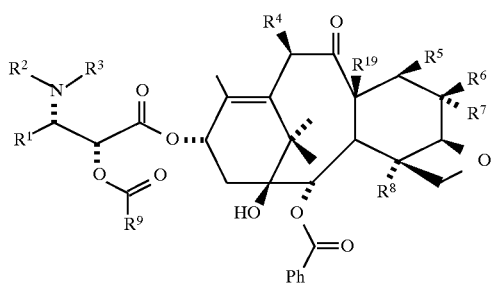

wherein
- $R^1$ is phenyl, p-fluorophenyl, isobutenyl, isobutyl, 2-furyl, cyclopropyl or isopropyl;
- $R^2$ is hydrogen and $R^3$ is —$SR^y$ in which $R^y$ is aryl, substituted aryl, heteroaryl, substituted heteroaryl or $C_{1-6}$ alkyl substituted by both a carboxyl and amino group;
- $R^4$ is —C(O)CH$_3$;
- $R^5$ is hydrogen, hydroxy, —OCH$_2$OCH$_3$, —OCH$_2$SCH$_3$ or —OC(O)OR$_a$ in which R$_a$ is $C_{1-6}$ alkyl;
- $R^6$ and $R^7$ are each independently hydrogen, hydroxy or —OCH$_2$OCH$_3$;
- $R^{19}$ is methyl or hydroxymethyl, or $R^{19}$ and $R^5$ together can form a cyclopropane ring in which case $R^6$ and $R^7$ are both hydrogen; and
- $R^8$ is

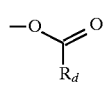

in which R$_d$ is $C_{1-6}$ alkyl, $C_{3-6}$ cycloalkyl or —O—$C_{1-6}$ alkyl; or a pharmaceutically acceptable salt thereof.

3. A compound of the formula

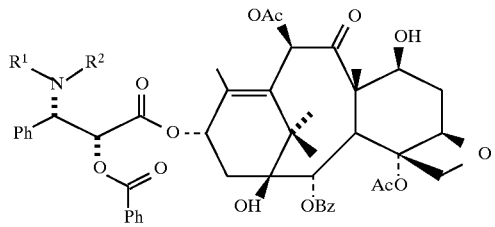

wherein $R^1$ and $R^2$ are either both

or $R^2$ is hydrogen and $R^1$ is

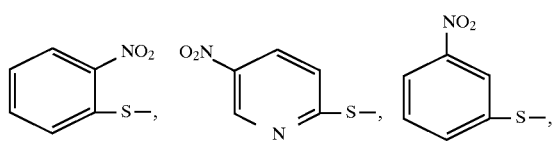

4. The compound of claim 3 wherein $R^2$ is hydrogen and $R^1$ is

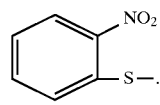

5. The compound of claim 3 wherein $R^2$ is hydrogen and $R^1$ is

6. The compound of claim 3 wherein $R^2$ is hydrogen and $R^1$ is

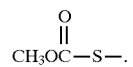

7. The compound of claim 3 wherein $R^2$ is hydrogen and $R^1$ is

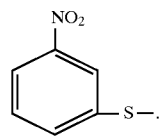

8. The compound of claim 3 wherein $R^2$ is hydrogen and $R^1$ is

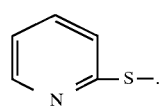

9. The compound of claim 3 wherein $R^1$ and $R^2$ are both

10. A pharmaceutical formulation which comprises an antitumor effective amount of a compound of claim 1 and a pharmaceutically acceptable carrier.

11. A method for inhibiting tumor growth in a mammalian host which comprises administering to said host a tumor growth inhibiting amount of a compound of claim 1.

* * * * *